United States Patent
Gill et al.

(10) Patent No.: US 7,529,580 B2
(45) Date of Patent: May 5, 2009

(54) DETECTION OF RENAL FAILURE BY CARDIAC IMPLANTABLE MEDICAL DEVICE

(75) Inventors: Jong Gill, Valencia, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 214 days.

(21) Appl. No.: 11/202,534

(22) Filed: Aug. 11, 2005

(65) Prior Publication Data

US 2007/0038138 A1 Feb. 15, 2007

(51) Int. Cl.
*A61B 5/02* (2006.01)

(52) U.S. Cl. .......................... 600/513; 600/509; 607/25

(58) Field of Classification Search ................ 600/509, 600/513, 13, 609; 607/25
See application file for complete search history.

(56) References Cited

U.S. PATENT DOCUMENTS

| | | | | |
|---|---|---|---|---|
| 6,016,443 A | 1/2000 | Ekwall et al. | ............... | 600/519 |
| 2003/0083585 A1 | 5/2003 | Van Oort et al. | ............ | 600/510 |
| 2003/0158492 A1* | 8/2003 | Sheldon et al. | ............. | 600/508 |
| 2004/0077962 A1 | 4/2004 | Kroll | .......................... | 600/513 |
| 2005/0234352 A1* | 10/2005 | Bardy | ........................ | 600/508 |

(Continued)

FOREIGN PATENT DOCUMENTS

EP 1543770 A1 6/2005

(Continued)

OTHER PUBLICATIONS

Shapira, Oz M. MD et al., "ECG Changes and Cardiac Arrhythmias in Chronic Renal Failure Patients on Hemodialysis", *Journal of Electrocardiology*, vol. 25, No. 4 (Oct. 1992), pp. 273-279.

(Continued)

*Primary Examiner*—Carl H Layno
*Assistant Examiner*—Deborah Malamud

(57) ABSTRACT

Morphological features within electrical cardiac signals are tracked and feature changes are monitored to detect renal failure. The morphological feature may be an interval between corresponding polarization events such as the interval between QRS-complexes and peaks of corresponding T-waves (QTmax interval); the interval between QRS-complexes and ends of corresponding T-waves (QTend interval); or the interval between P-waves and corresponding QRS-complexes (PR interval). The feature may also be the elevation of a cardiac signal segment between corresponding polarization events, such as QRS-complexes and corresponding T-waves (ST segment); a duration of a polarization event, such as a QRS-complex (QRS width); or an amplitude of a polarization event, such as a T-wave (T-wave amplitude). The change in the feature may comprise a decrease in QTmax intervals, a decrease in QTend intervals, a deviation in ST segment elevation, an increase in QRS width, an increase in PR interval or a deviation in T-wave amplitude.

9 Claims, 18 Drawing Sheets

U.S. PATENT DOCUMENTS

| | | | | |
|---|---|---|---|---|
| 6,256,538 B1 | 7/2001 | Ekwall | ........................ | 607/17 |
| 6,368,284 B1 | 4/2002 | Bardy | | |
| 6,671,549 B2 * | 12/2003 | Van Dam et al. | ............... | 607/25 |
| 6,695,790 B2 | 2/2004 | Van Oort et al. | ............ | 600/508 |

FOREIGN PATENT DOCUMENTS

| | | | |
|---|---|---|---|
| WO | 2006081336 A2 | 8/2006 | |

OTHER PUBLICATIONS

Madias, J. E., "The impact of Change Oedematous States on the QRS Duration: Implications for Cardiac Resynchronization Therapy and Implantable Cardioverter/Defibrillator Implantation", *Europace* (Mar. 2005); 7(2), pp. 158-164.

Arthur, Wayne et al., "Hyperkalemia Diagnosed by Implantable Cardioverter Defibrillator T Wave Sensing," PACE May 2001;24:908-909.

NonFinal Office Action, mailed Aug. 28, 2007: Related U.S. Appl. No. 11/202,553.

European Search Report, dated Nov. 13, 2006: EP Application No. 06254244.4.

* cited by examiner

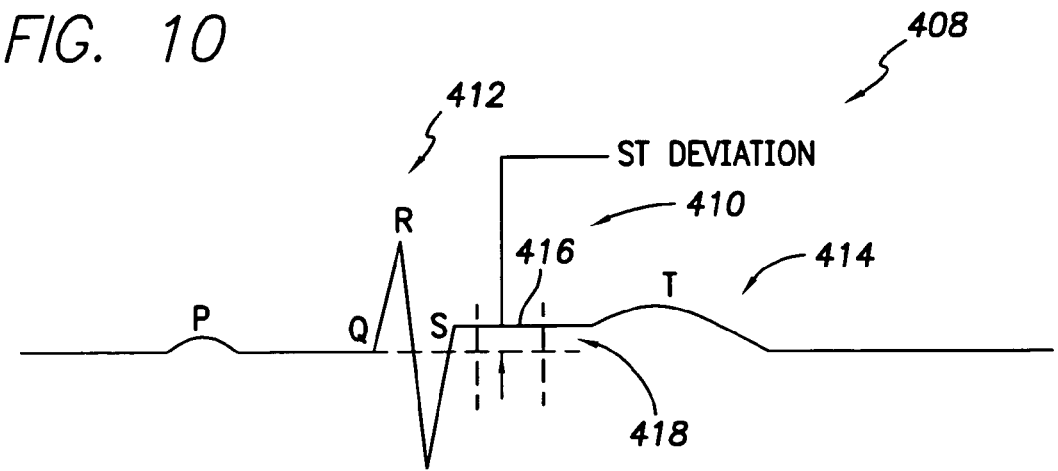
FIG. 10
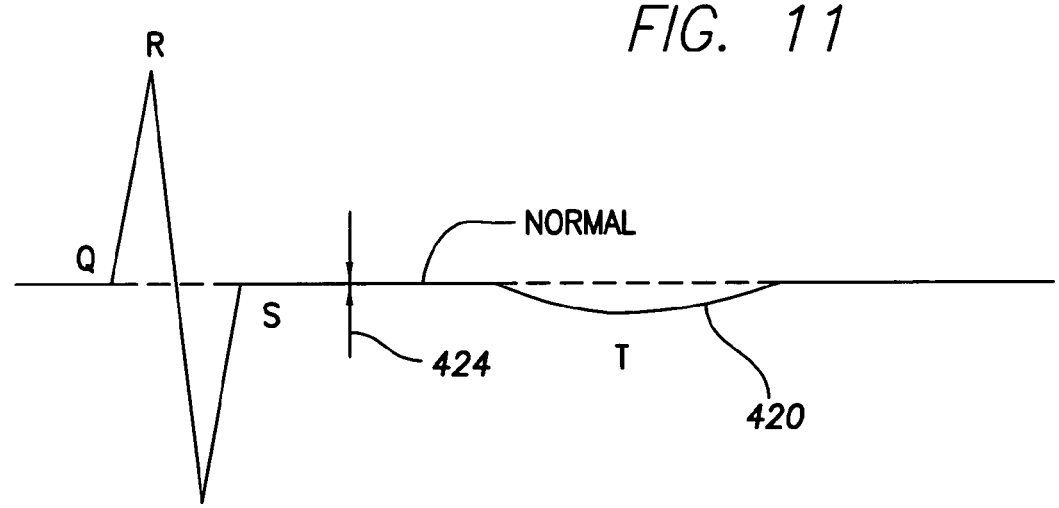
FIG. 11
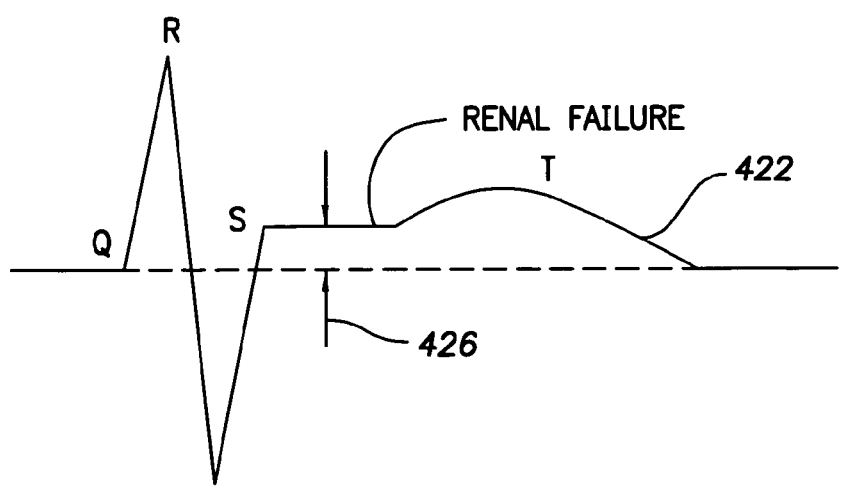

DETECTION OF RENAL FAILURE BY CARDIAC IMPLANTABLE MEDICAL DEVICE

CROSS REFERENCE TO RELATED APPLICATIONS

This application is related to copending U.S. patent application Ser. No. 11/202,553, filed Nov. 11, 2005, titled "Detection of Renal Failure by Cardiac Implantable Medical Device".

FIELD OF THE INVENTION

The invention relates generally to cardiac implantable medical devices and more particularly to cardiac implantable medical devices that monitor for and detect renal failure.

BACKGROUND

Cardiac rhythm management (CRM) devices are well known in the art. They include implantable pacemakers which provide stimulation pulses to a heart to cause a heart, which would normally or otherwise beat too slowly or at an irregular rate, to beat at a controlled normal rate. They also include defibrillators which detect when the atria and/or the ventricles of the heart are in fibrillation and apply cardioverting or defibrillating electrical energy to the heart to restore the heart to a normal rhythm. Implantable cardiac devices may also include the combined functionalities of a pacemaker and a defibrillator.

Implantable cardiac stimulation devices sense cardiac activity for monitoring the cardiac condition of the patient in which the device is implanted. By sensing the electrical cardiac activity of the patient, the device is able to provide cardiac stimulation therapy when it is required. The sensed cardiac activity may also be used to monitor for and detect other cardiac conditions such as cardiac ischemia.

It has been recognized that knowledge of electrical activity of the heart may provide significant insight into the existence of non-cardiac conditions such as hypoglycemia (low blood sugar levels) and hyperglycemia (high blood sugar levels). Such uses of sensed cardiac activity is disclosed in U.S. patent application Ser. No. 11/043,612, filed Jan. 25, 2005, entitled "System and Method for Distinguishing Among Cardiac Ischemia, Hypoglycemia and Hyperglycemia Using An Implantable Medical Device," of Kil et al.

Those skilled in the art have thus recognized the possibility of detecting non-cardiac conditions using sensed cardiac electrical activity. The invention advances this recognition by using cardiac electrical activity to monitor for and detect renal failure.

SUMMARY

Briefly, and in general terms, what are described herein are methods of, and systems for, detecting renal failure using electrical cardiac signals that are obtained using an implantable medical device, such as a pacemaker or implanted cardiac defibrillator.

In one aspect, a method is described for detecting renal failure in a patient using an implanted medical device. The method includes tracking a morphological feature within electrical cardiac signals and detecting renal failure based on a change in the feature.

The morphological feature may be an interval between corresponding polarization events such as the interval between QRS-complexes and peaks of corresponding T-waves (QTmax interval); the interval between QRS-complexes and ends of corresponding T-waves (QTend interval); or the interval between P-waves and corresponding QRS-complexes (PR interval). The morphological feature may also be the elevation of a segment of a cardiac signal between corresponding polarization events, such as QRS-complexes and corresponding T-waves (ST segment); a duration of a polarization event, such as a QRS-complex (QRS width); or an amplitude of a polarization event, such as a T-wave (T-wave amplitude). The change in the feature may comprise a decrease in QTmax intervals, a decrease in QTend intervals, a deviation, i.e., either an increase or a decrease, in ST segment elevation, an increase in QRS width, an increase in PR interval or a deviation in T-wave amplitude.

In another aspect, a system is described for detecting renal failure. The system includes a tracking unit that is operative to track a morphological feature within electrical cardiac signals that are obtained using an implantable medical device. The system also includes a renal failure detection unit that is operative to detect renal failure based on a change in the feature.

These and other aspects and advantages of the invention will become apparent from the following detailed description and the accompanying drawings which illustrate by way of example the features of the invention.

BRIEF DESCRIPTION OF THE DRAWINGS

FIG. 10 is a graph providing a stylized representation of the IEGM of a single heartbeat illustrating the ST segment;

FIG. 11 is a graph providing exemplary representations of the IEGM of a single heart beat illustrating a deviation, in this case an increase, in ST segment elevation associated with renal failure;

DETAILED DESCRIPTION

The following description includes the best mode presently contemplated for practicing the invention. The description is not to be taken in a limiting sense but is made merely for the purpose of describing the general principles of the illustrative embodiments. The scope of the invention should be ascertained with reference to the claims. In the description that follows, like numerals or reference designators will be used to refer to like parts or elements throughout.

Overview of Implantable Device

Figure 1:
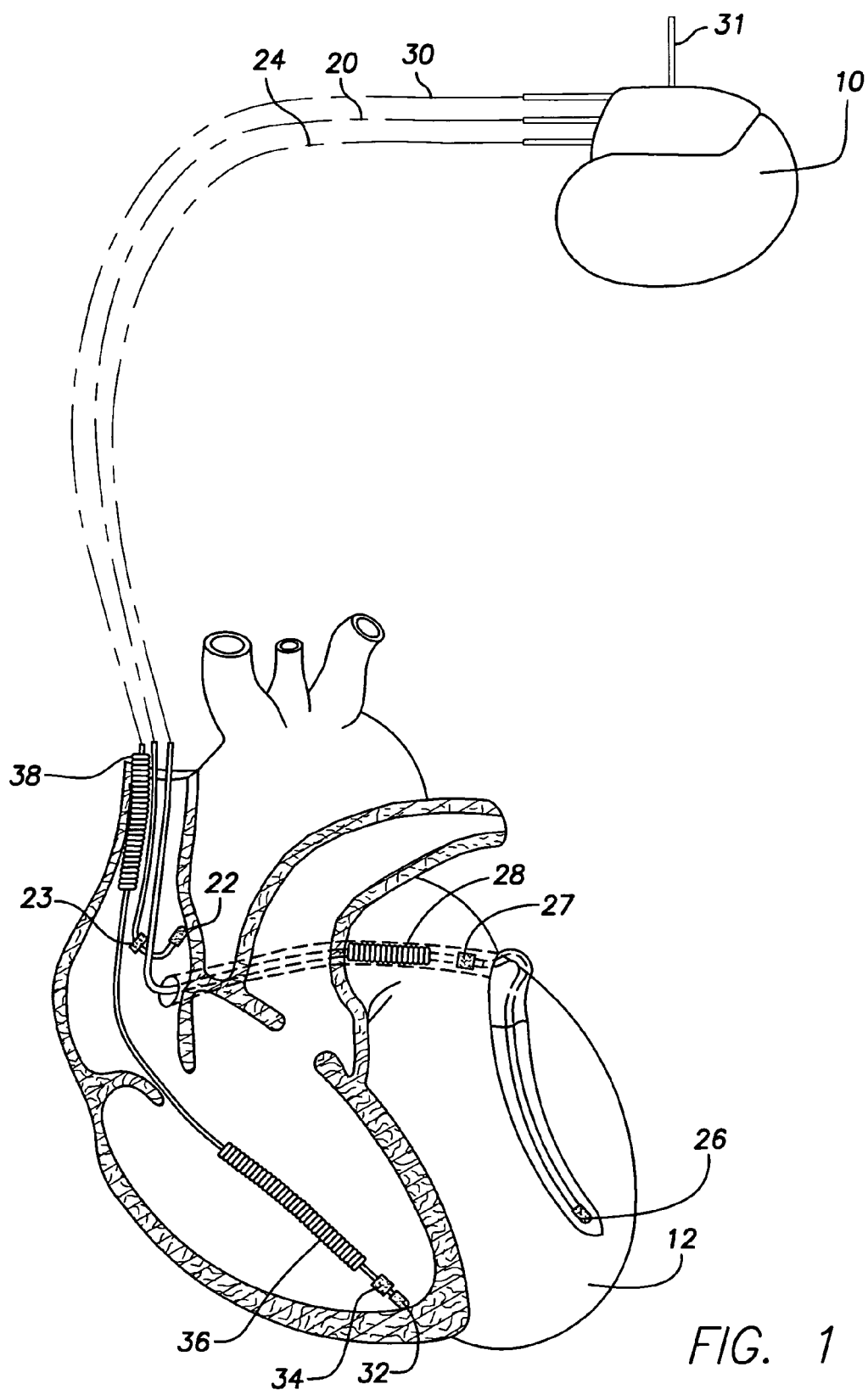
FIG. 1 is a simplified diagram illustrating an implantable cardiac medical device with at least three leads implanted in the heart of a patient for delivering multi-chamber stimulation and shock therapy.

With reference to FIG. 1, there is a stimulation device 10 in electrical communication with the heart 12 of a patient by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the right atrial appendage and an atrial ring electrode 23. To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the heart by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart so as to place the right ventricular tip electrode 32 in the right ventricular apex so that the RV coil electrode is positioned in the right ventricle and the SVC coil electrode 38 is positioned in the superior vena cava. Accordingly, the right ventricular lead 30 is capable of receiving cardiac signals, and delivering stimulation in the form of pacing and shock therapy to the right ventricle. To provide a "tickle warning" signal, an additional electrode 31 is provided in proximity to the device can.

Figure 2:
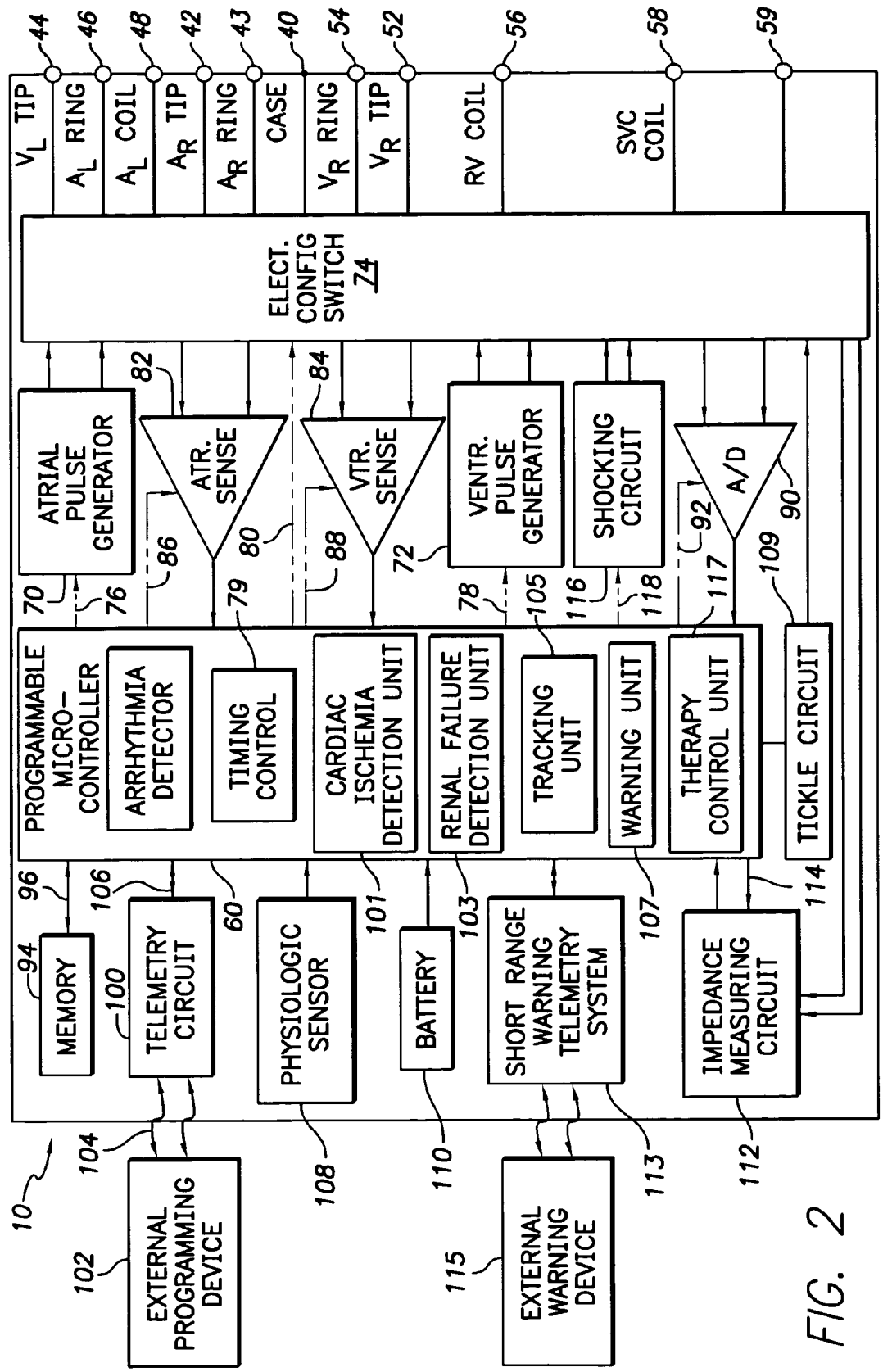
FIG. 2 is a functional block diagram of the implantable cardiac medical device of FIG. 1 illustrating basic elements of the device, including components for detecting renal failure.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 43, 44, 46, 48, 52, 54, 56 and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22 and a right atrial ring ($A_R$ RING) electrode 43 adapted for connection to right atrial ring electrode 23. To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively. To support right chamber sensing, pacing and shocking, the connector further includes a right ventricular tip terminal ($V_R$ TIP) 52, a right ventricular ring terminal ($V_R$ RING) 54, a right ventricular shocking terminal (RV COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively. To provide the "tickle warning" signal, an additional terminal 59 is provided for connection to the tickle warning electrode 31 of FIG. 1.

At the core of the stimulation device 10 is a programmable microcontroller 60, which controls the various modes of stimulation therapy. As is well known in the art, the microcontroller 60 (also referred to as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers or shared amplifiers. The switch 74 determines the "sensing polarity" of the cardiac signal by selectively closing the appropriate switches, as is also known in the art. In this way, the clinician may program the sensing polarity independent of the stimulation polarity. Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. Other pacing parameters include base rate, rest rate and circadian base rate.

Advantageously, the operating parameters of the implantable device 10 may be non-invasively programmed into the memory 94 through a telemetry circuit 100 in telemetric communication with the external device 102, such as a programmer, transtelephonic transceiver or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses. While shown as being included within the stimulation device 10, it is to be understood that the physiologic sensor 108 may also be external to the stimulation device 10, yet still be implanted within or carried by the patient.

The stimulation device additionally includes a battery 110, which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices. As further shown in FIG. 2, the device 10 is shown as having an impedance measuring circuit 112, which is enabled by the microcontroller 60 via a control signal 114.

In the case where the stimulation device 10 is intended to operate as an implantable cardioverter/defibrillator (ICD) device, it detects the occurrence of an arrhythmia and automatically applies an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Finally, with regard to FIG. 2, microcontroller 60 includes a tracking unit 105 for tracking various morphological features within electrical cardiac signals, including intervals between polarization events, elevations between polarization events, durations of polarization events and amplitudes of polarization events. The microcontroller also includes a cardiac ischemia detection unit 101 for controlling the detection of episodes of cardiac ischemia and a renal failure detection unit 103 for controlling the detection of episodes of renal failure, each based on changes in the features tracked by the tracking unit 105. A warning unit 107 controls delivery of warning signals to the patient indicative of ischemia or renal failure. In particular, warning unit 107 controls a tickle circuit 109 that generates subcutaneous perceptible warning signals via lead 31 (FIG. 1), which is connected via connector 59. Device case electrodes 40 may be used as the return electrode for the tickle warning signal. Thereafter, warning unit 107 controls a short-range telemetry system 113 to transmit warning signals to an external handheld warning device 115 for confirmation. Additionally, a therapy control unit 117 may be provided to control therapy based upon the detection of ischemia or renal failure. The operation of these devices will be described below with reference to the remaining figures.

Referring to the remaining figures, flow charts, graphs and other diagrams illustrate the operation and novel features of stimulation device 10 as configured in accordance with exemplary embodiments of the invention. In the flow charts, the various algorithmic steps are summarized in individual "blocks". Such blocks describe specific actions or decisions made or carried out as the algorithm proceeds. Where a microcontroller (or equivalent) is employed, the flow charts provide the basis for a "monitoring/detection program" that may be used by such a microcontroller (or equivalent) to monitor for and detect renal failure. Those skilled in the art may readily write such a program based on the flow charts and other descriptions presented herein.

Overview of Renal Failure Detection Based on Changes in EGM

Among the numerous effects caused by renal failure, the one that affects the electrophysiology of cardiac myocytes the most is hyperkalemia. The clinical manifestation of hyperkalemia, especially on cardiovascular systems, is a membrane depolarization with decreased conduction velocity and a faster rate of membrane repolarization. These manifestations may lead to changes in ECG such as those listed in the following table:

| Feature | Change associated with renal failure |
| --- | --- |
| QTmax interval | Decrease |
| QTend interval | Decrease |
| ST segment elevation | Decrease/Increase |
| QRS width | Increase |
| PR interval | Increase |
| T wave amplitude | Decrease/Increase |

In accordance with the invention, the morphological changes typically observed in ECG are extracted from intracardiac electrograms (EGM). By monitoring the changes in one or more of the above morphological features available in EGM, renal failure can be detected. Following are descriptions of each of the above features and the processes by which renal failure is detected based on changes in the features.

Renal Failure Detection Based on QTmax

Figure 3:
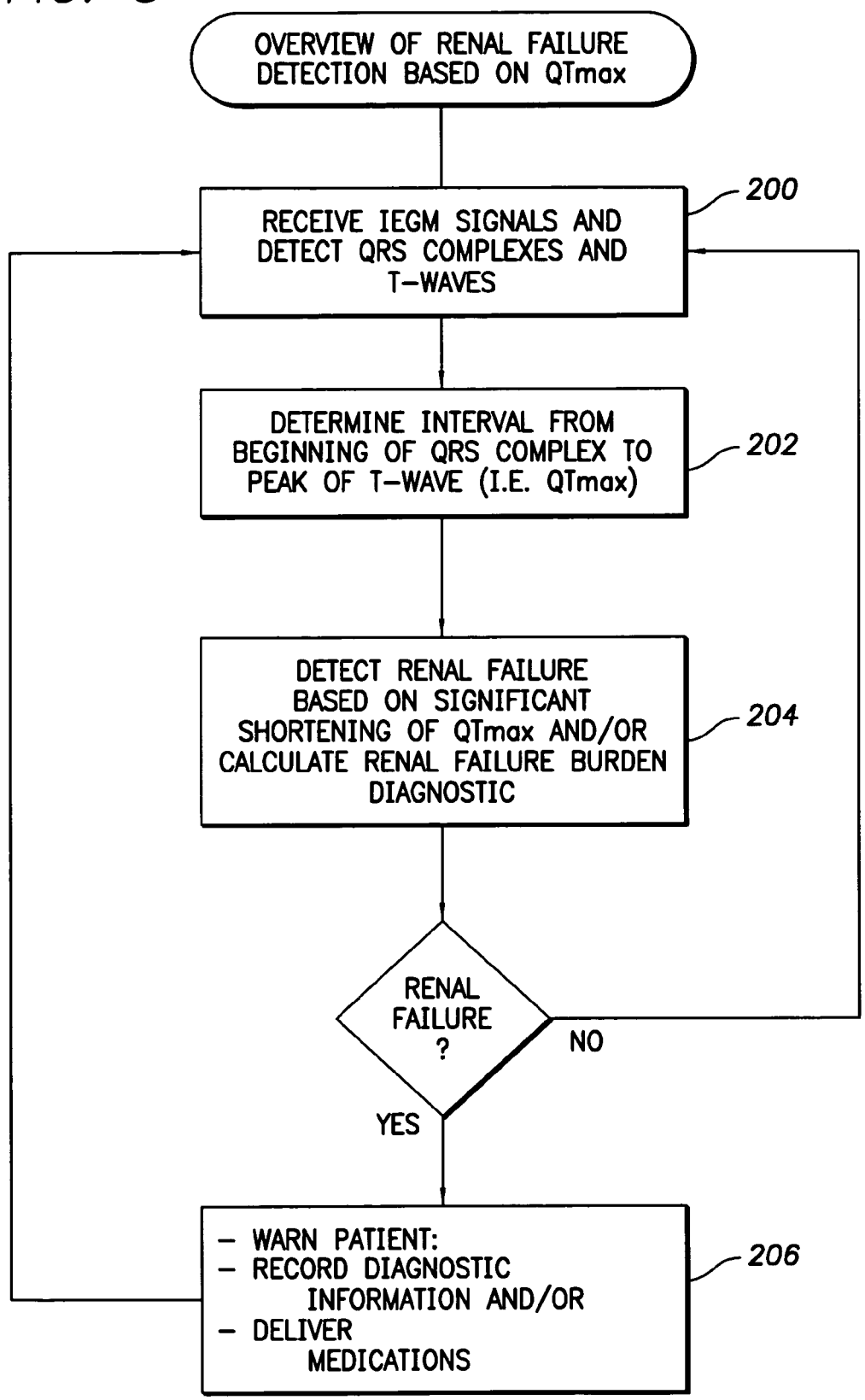
FIG. 3 is a flow chart providing an overview of an exemplary method performed by the device of FIG. 2 for detecting renal failure based on a decrease in QTmax.

FIG. 3 provides an overview of a QTmax-based renal failure detection technique performed by the device of FIG. 2. Initially, at step 200, IEGM signals are received and QRS-complexes and T-waves are identified. At step 202, the interval from the beginning of the QRS complex to the peak or maximum absolute amplitude of the T-wave is calculated. This interval is referred to as QTmax. The Q wave of the QRS complex may be identified as the point within the QRS complex where the IEGM signal exceeds a threshold value set based on the maximum amplitude of the QRS complex itself. The maximum of the T-wave may be identified as the maximum point within a T-wave interval beginning 250 ms following the Q wave of the QRS complex and extending for 200 ms. These are merely exemplary values. At step 204, renal failure is detected based upon detection of a significant shortening of QTmax. Routine experimentation may be performed to determine what constitutes "significant" insofar as changes in QTmax are concerned (and insofar as any other changes referred to herein as being "significant" are concerned.) In one example, a 10% or greater change in a given parameter is deemed to be significant. Note that QTmax values may be derived from either paced or sensed events but values derived from paced and sensed events should not be combined. In addition, QTmax varies with heart rate and so should be normalized based on heart rate. Bazette's equation may be used for normalizing QTmax (and for normalizing other parameters discussed.)

Additionally, or in the alternative, at step 204, the device calculates a "renal failure burden" based on QTmax, which is representative of the proportion of the time renal failure is detected. In one example, the renal failure burden is a numerical value representative of the extent to and/or the time during which QTmax is shorter than its running average. If QTmax is measured for diagnostic purposes only, steps 200-204 are preferably performed once an hour to calculate and record renal failure burden. If measured for detecting renal failure, steps 200-204 are preferably performed once every 30 seconds.

In any case, so long as no renal failure is detected, steps 200-204 are merely repeated. If renal failure is detected, however, the patient is warned of the renal failure by application of an internal perceptible "tickle" notification signal, at step 206. If the device is configured to generate warning signals for other conditions, such as cardiac ischemia, the device preferably employs different notification signal frequencies for the different warnings so that the patient can properly distinguish between different warnings. In addition, warning signals may be transmitted using a short-range telemetry system to a handheld warning device using techniques described, for example, in U.S. patent application Ser. No. 10/603,429, entitled "System And Method For Detecting Cardiac Ischemia Using An Implantable Medical Device," of Wang et al., filed Jun. 24, 2003, which is incorporated by reference. The handheld warning device thereby provides confirmation of the warning to the patient, who may be otherwise uncertain as to the reason for the internally generated tickle warning signal. Additionally, if so equipped, the device may automatically control therapy in response to the hyperkalemia. For example, if a drug pump is implanted within the patient, the pump may be controlled to deliver suitable drugs. Exemplary drugs are the ones which can provide the following or combination of following actions such as lowering blood pressure, increase in red blood cell production and Vitamin D supplement.

As will be explained below, additional parameters of the IEGM signal, such as QTend, ST deviation, QSR width, PR interval and T-wave amplitude may be employed to confirm a detection made based upon QTmax. Insofar as the detection of T-waves at step 200 is concerned, the invention may exploit techniques set forth in U.S. Patent Application Serial Number 2004/0077962 of Kroll, published Apr. 22, 2004, entitled "System and Method for Monitoring Blood Glucose Levels Using an Implantable Medical Device." Certain techniques described therein are particularly well suited for detecting T-waves with a high degree of accuracy to permit precise detection of features of the T-wave (such as its peak) so as to achieve more precise measurement of QRS/T-wave intervals. The patent application to Kroll is fully incorporated by reference. The invention also may exploit T-wave detection techniques set forth in U.S. patent application Ser. No. 10/603, 398, entitled "System and Method for Detecting Cardiac Ischemia Based on T-Waves Using an Implantable Medical Device," of Min et al., filed Jun. 24, 2003, which is also incorporated by reference.

Figure 4:
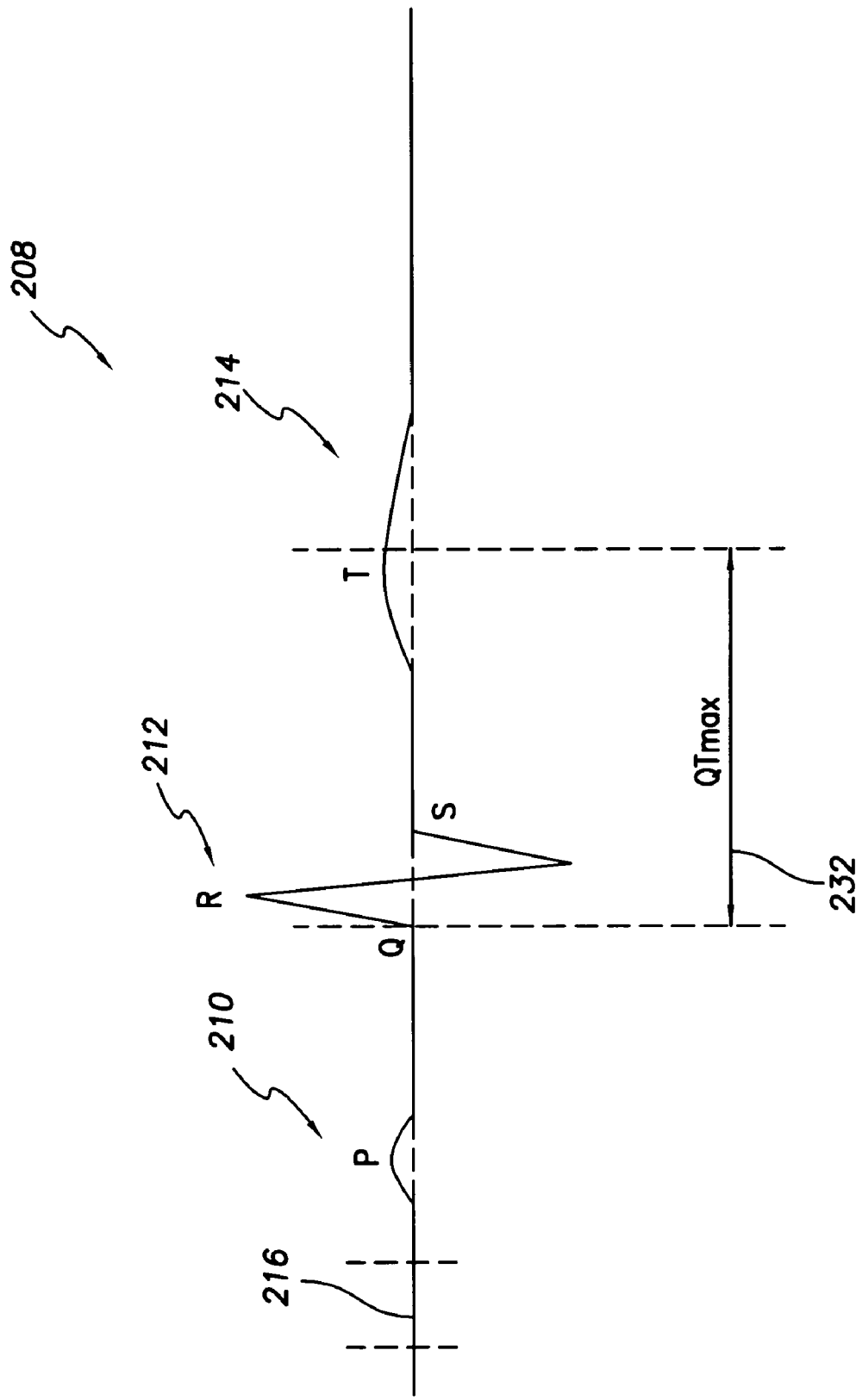
FIG. 4 is a graph providing a stylized representation of the IEGM of a single heartbeat illustrating the QTmax interval.

FIG. 4 illustrates the QTmax interval 232. Briefly, the figure provides a stylized representation of an exemplary IEGM trace 208 for a single healthy heartbeat. The stylized representation of the IEGM signal of FIG. 4 is provided for illustrative purposes and should not be construed as an actual, clinically detected IEGM signal. The heartbeat includes a P-wave 210 representative of an atrial depolarization, a QRS complex 212 representative of a ventricular depolarization and a T-wave 214 representative of ventricular repolarization.

The QRS complex 212 itself is defined by points Q, R, and S. Q represents the beginning of the complex; R represents the peak of the complex; and S represents the end of the complex. In the examples described and illustrated herein, the aforementioned QTmax interval is specified as the time interval from point Q to the peak or maximum amplitude point of T-wave 214. However, QTmax may alternatively be calculated based on other points or features of the QRS complex 212, such as the R point or the S point of the complex, so long as the calculations are consistent.

As used, the "Q" of QTmax generally refers to the QRS complex 212 and not specifically to the Q point of the QRS complex. Thus, the term QTmax encompasses RTmax as one example and STmax as another example. Also, in the particular example of FIG. 4, the peak of the T-wave 214 is positive, i.e. it is greater than a baseline voltage of the IEGM signal 208. This need not be the case. In other examples, the peak has a negative value with respect to a baseline of the IEGM signal 208. The polarity of the entire signal may also be reversed. The peak or maximum amplitude of T-wave 214 refers to the peak or maximum of the absolute value of the difference between the T-wave voltage and the baseline voltage of the IEGM signal 208. The baseline voltage 216 may be measured during an interval prior to the P-wave 210, as shown. The interval may be, for example, 50 milliseconds (ms) in duration, beginning 100 ms prior to the P-wave 210. Alternatively, the interval may be timed relative to the QRS complex 212. If timed relative to the QRS complex 212, the interval may commence 250 ms prior to the R wave of the QRS complex. Also alternatively, a single detection point may be used, rather than a detection interval.

Figure 5:
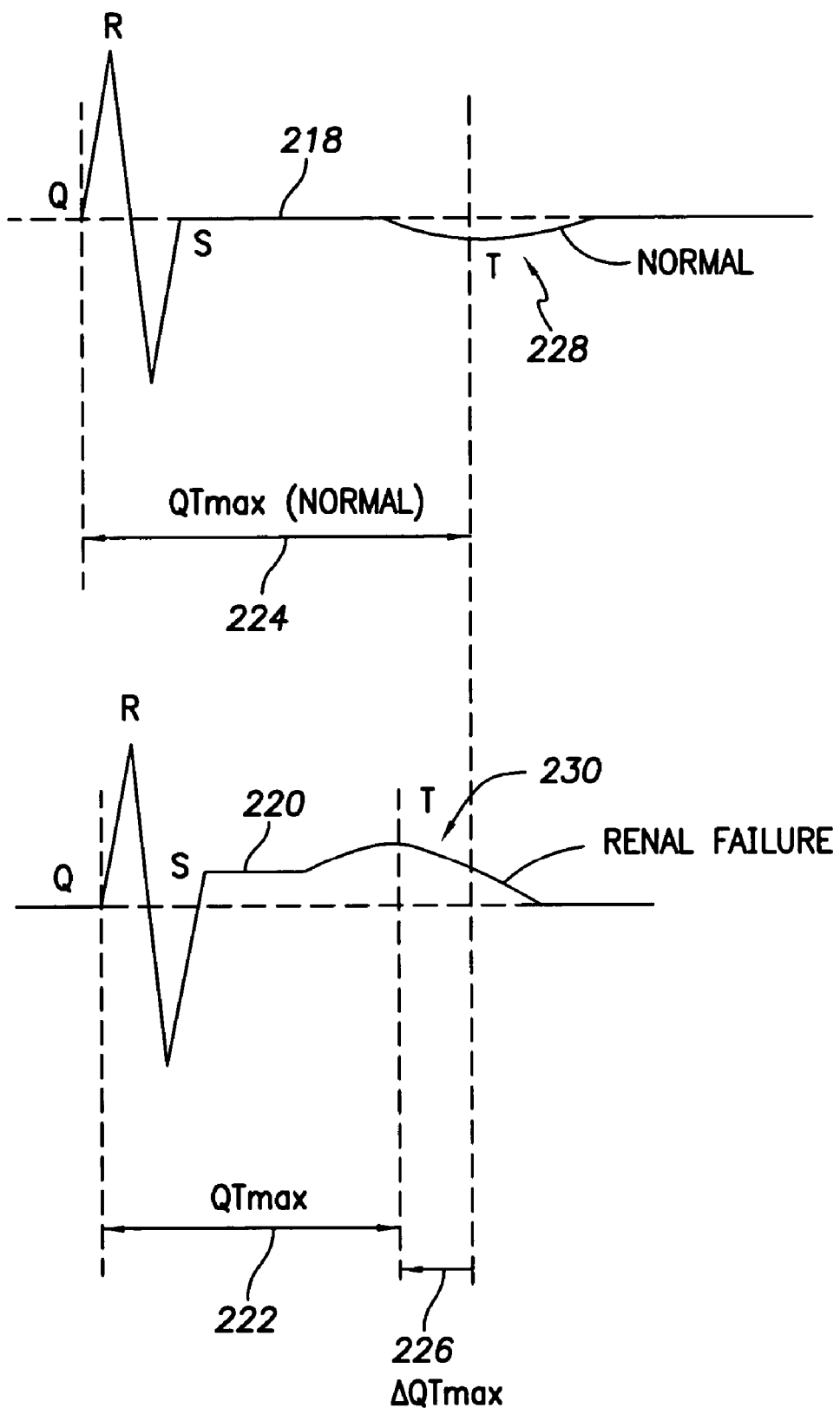
FIG. 5 is a graph providing exemplary representations of the IEGM of a single heart beat illustrating a reduction in the QTmax interval associated with renal failure.

FIG. 5 illustrates change in QTmax brought on by renal failure. A first exemplary IEGM trace 218 represents a heartbeat of a healthy patient, i.e. one not subject to renal failure. A second trace 220 illustrates the heartbeat for a patient suffering renal failure. The traces are IEGM signals derived from voltage differences between the tip of a right ventricular (RV) lead and the device case. Note first that the IEGM trace for the healthy patient exhibits a T-wave 228 that is reversed in polarity with respect to T-wave 230 of the patient suffering renal failure. T-wave inversion may exist during renal failure. Therefore, FIG. 5 illustrates that the QTmax feature is valid even in the presence of a T-wave inversion. In any case, for the purposes of renal failure detection, the peak of the T-wave 230 during renal failure occurs earlier than the corresponding peak 228 without renal failure. In other words, QTmax during renal failure 222 is shorter than QTmax without renal failure 224. Hence, a large positive value of ΔQTmax 226 is observed, where ΔQTmax represents the amount of the reduction in QTmax. A negative value of ΔQTmax is associated with an increase in interval length. In the example FIG. 5, ΔQTmax is represented as a positive number.

ΔQTmax is the value used to detect renal failure. Preferably, any change in QTmax from a current baseline value is tracked. In one example, the device tracks a running average of QTmax intervals (derived from sensed events and normalized based on heart rate) for use as a baseline value. Different baseline values may be calculated for different heart rate ranges. In any case, for each new heartbeat, the device compares the QTmax interval for that heartbeat against the appropriate baseline to calculate ΔQTmax for that heartbeat. ΔQTmax values are averaged over a number of heartbeats, e.g., eight to sixteen, and then compared against a predetermined QTmax-based threshold. If the average exceeds the threshold, renal failure is thereby indicated.

The threshold is a programmable value set, for example, based upon a percentage of the running average of the QTmax interval. In one specific example, if ΔQTmax is a positive value, which exceeds 10% of the running average of the QTmax intervals, renal failure is thereby indicated (i.e. QTmax has been found to be reduced by 10%). Otherwise conventional threshold comparison techniques may be employed for use with ΔQTmax. In another example, rather than comparing an average based on eight to sixteen values to the threshold, the occurrence of only a single ΔQTmax value exceeding the threshold is indicative of renal failure. In yet another example, if ΔQTmax exceeds the threshold for three out of five heartbeats, renal failure is indicated. Multiple thresholds may be defined, if desired, to trigger warning signals indicative of different levels of urgency. For example, if ΔQTmax exceeds a first, lower threshold, a warning signal indicative of a moderate renal failure is issued. If ΔQTmax exceeds a higher threshold, a second warning signal indicative of a more serious renal failure is issued. As can be appreciated, a wide variety of specific implementations may be provided in accordance with the general techniques described. Routine experimentation may be performed to determine appropriate threshold levels.

Renal Failure Detection Based on QTend

Figure 6:
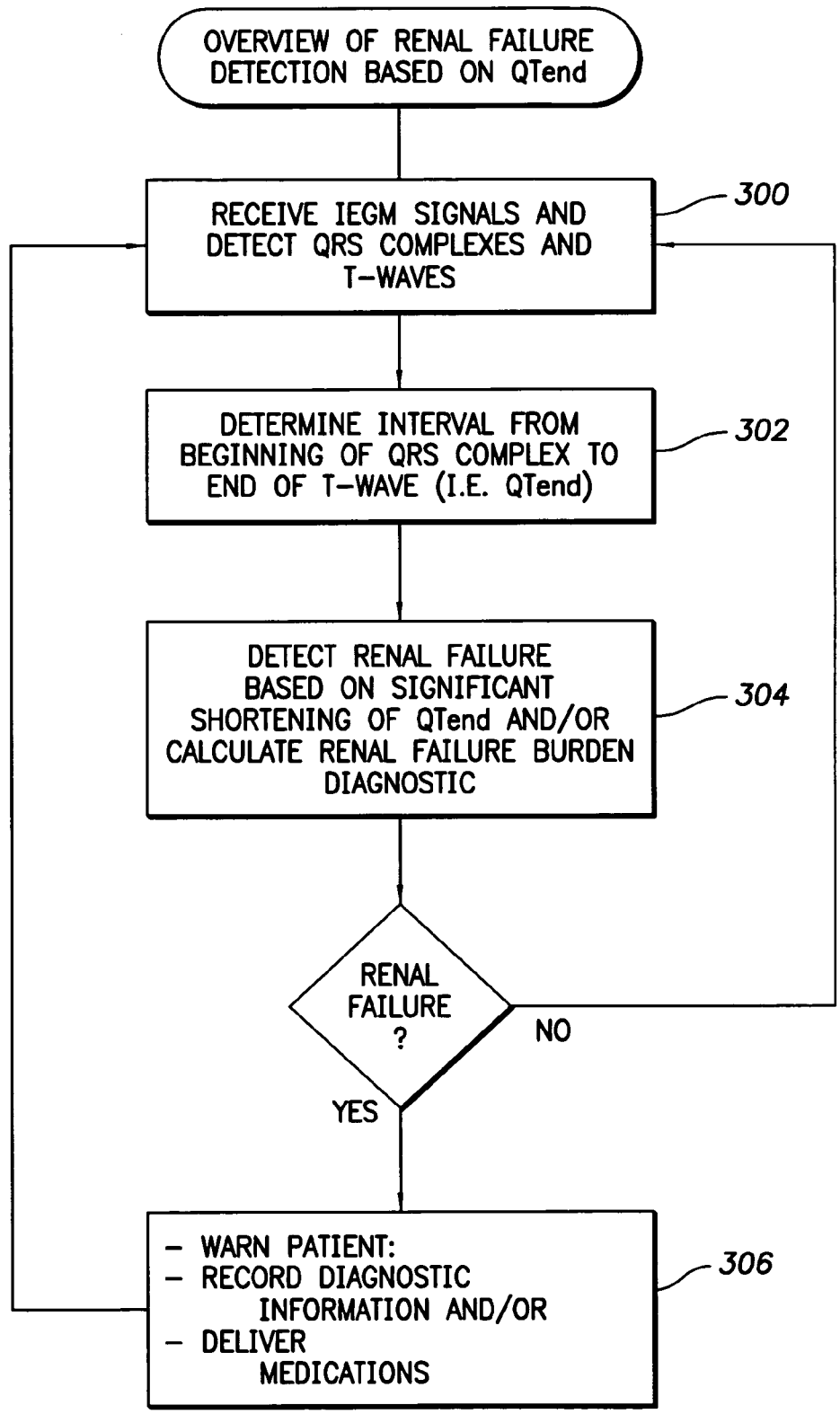
FIG. 6 is a flow chart providing an overview of an exemplary method performed by the device of FIG. 2 for detecting renal failure based on a decrease in QTend.

FIG. 6 provides an overview of a QTend-based renal failure detection technique performed by the device of FIG. 2. Many aspects of the technique are similar to those of the technique of FIG. 3 and will not be described again in detail. Initially, at step 300, IEGM signals are received and QRS-complexes and T-waves are identified. At step 302, the interval from the beginning of the QRS complex to the end of the T-wave is calculated. This interval is referred to as QTend. In the examples described and illustrated, the QTend interval is specified as the time interval from point Q of the QRS complex to the end point of the T-wave. However, as with QTmax, QTend may alternatively be calculated based on other points or features of the QRS complex, such as the R point or the S point of the complex, so long as the calculations are consistent. At step 304, renal failure is detected based upon observation of a significant shortening in QTend. As before, data from paced and sensed events should not be combined. QTend values should be normalized based on heart rate.

Additionally, or in the alternative, at step 304, the device calculates a "renal failure burden" based on QTend, which is representative of the proportion of time renal failure is detected. In one example, the renal failure burden is a numerical value representative of the extent to and/or time during which QTend is shorter than its running average. If QTend is measured for diagnostic purposes only, steps 300-304 are preferably performed once an hour to calculated and record the renal failure burden. If measured for detecting renal failure, steps 300-304 are preferably performed more often, e.g. once every 30 seconds.

In any case, so long as no renal failure is detected, steps 300-304 are merely repeated. If renal failure is detected, however, the patient is warned of the renal failure, at step 306, and, if so equipped, the device automatically controls therapy in response to the renal failure.

Figure 7:
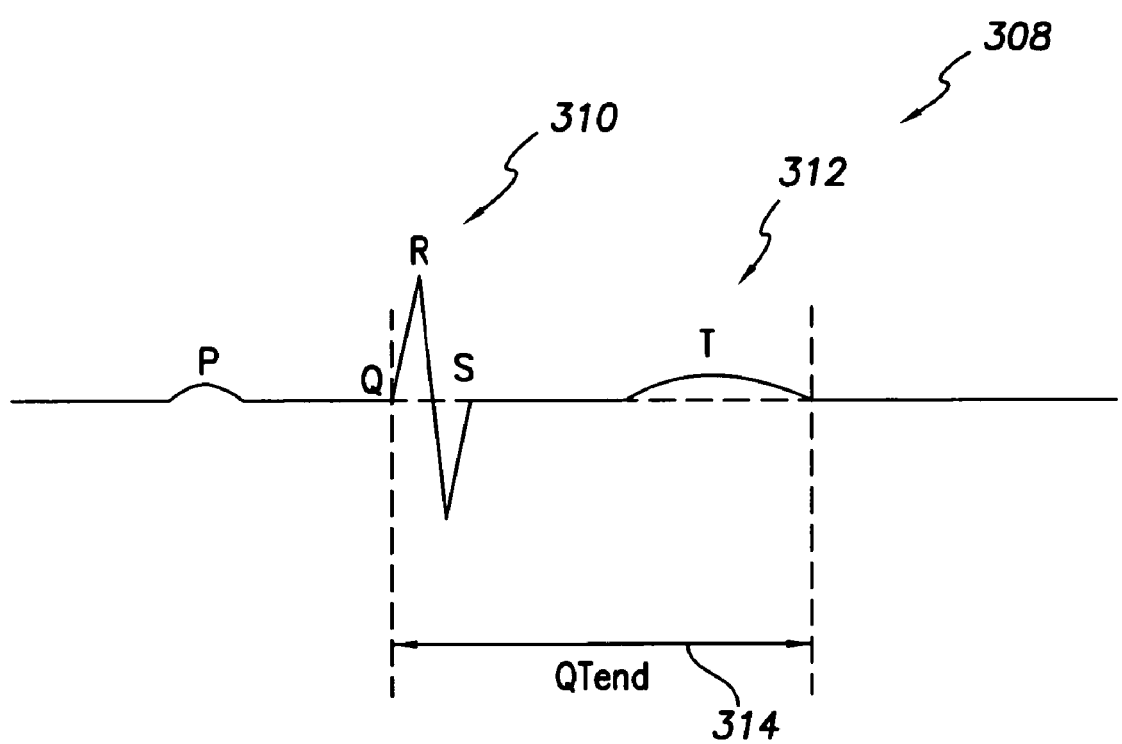
FIG. 7 is a graph providing a stylized representation of the IEGM of a single heartbeat illustrating the QTend interval.

FIG. 7 illustrates the QTend interval 314. Briefly, FIG. 7 provides a stylized representation of an exemplary IEGM trace 308 for a single healthy heartbeat. The QTend interval 314 is the time interval between the beginning of the QRS complex 310 and the end point of the T-wave 312, i.e. the point at which the slope of the T-wave following its peak becomes substantially flat. Techniques for detecting T-wave slope are set forth in the aforementioned patent application to Min et al.

Figure 8:
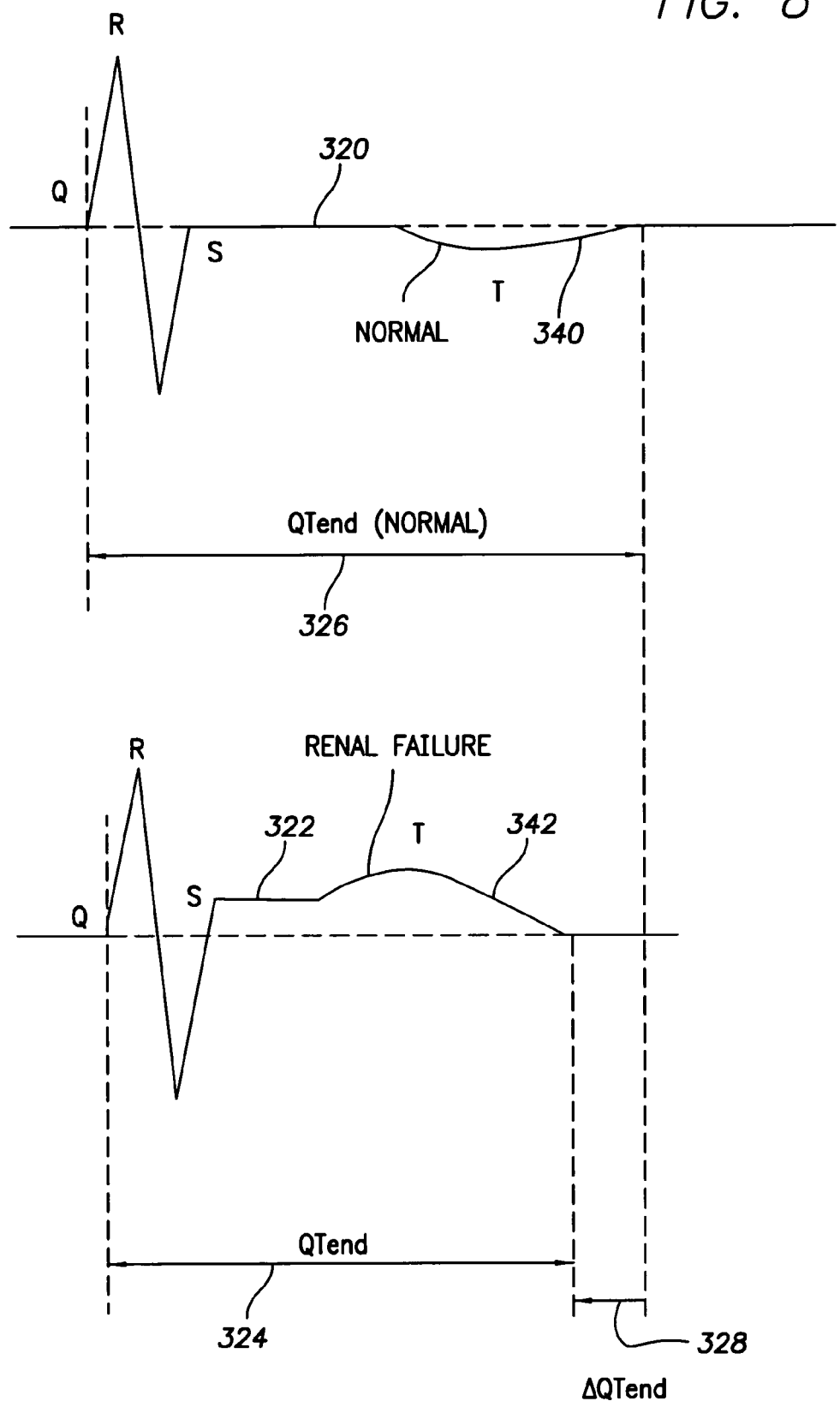
FIG. 8 is a graph providing exemplary representations of the IEGM of a single heart beat illustrating a reduction in the QTend interval associated with renal failure.

FIG. 8 illustrates changes in QTend brought on by renal failure. A first exemplary IEGM trace 320 represents a heartbeat of a healthy patient, i.e. one not subject to renal failure. A second trace 322 illustrates the heartbeat for a patient suffering renal failure. As with other traces illustrated, the IEGM signals of FIG. 8 are exemplary representations of IEGM signals provided for illustrative purposes only. For the purposes of renal failure detection, the end of the T-wave 342 during renal failure occurs earlier than the corresponding end of the T-wave 340 without renal failure. In other words, QTend during renal failure 324 is shorter than QTend without renal failure 326. Hence, a large positive value of ΔQTend 328 is observed, where ΔQTend represents the amount of the reduction in QTend. A negative value of ΔQTend is associated with an increase in interval length, which would not be indicative of renal failure.

ΔQTend is the value used to detect renal failure. Preferably, any changes in QTend from current baseline values are tracked. In one example, the device tracks a running average of the QTend interval (as derived from sensed events and normalized based on heart rate) and then, for each new heartbeat, compares the QTend interval for that heartbeat against the running average to calculate a ΔQTend value for that heartbeat. If the average exceeds the threshold, then the absolute value of ΔQTend is also averaged over eight to sixteen heartbeats and compared against a predetermined ΔQTend-based threshold. If ΔQTend exceeds its respective threshold, then renal failure is thereby indicated.

The various thresholds are programmable values set, for example, based upon respective running averages. In one specific example, the threshold for ΔQTend is set to 10% of the running average of the QTend intervals. As with the QTmax-based technique, alternative threshold comparison techniques may instead be used. Multiple thresholds may be defined, in some implementations, to trigger warning signals indicative of different levels of urgency. Routine experimentation may be performed to determine appropriate threshold levels.

As previously mentioned, a decrease in QTmax may be indicative of renal failure. It may, however, also be indicative of cardiac ischemia, as explained in U.S. patent application Ser. No. 11/043,612, entitled "System and Method for Distinguishing Among Cardiac Ischemia, Hypoglycemia and Hyperglycemia Using An Implantable Medical Device," of Kil et al., filed on Jan. 25, 2005. Kil et al. also explains that little or no change in QTend is observed during cardiac ischemia. Thus, in accordance with the present invention, a decrease in QTend corroborates a detection of renal failure that may be made based on a decrease in QTmax and distinguishes a decrease in QTmax caused by ischemia from a decrease caused by renal failure.

Renal Failure Detection Based on ST Segment Elevation

Figure 9:
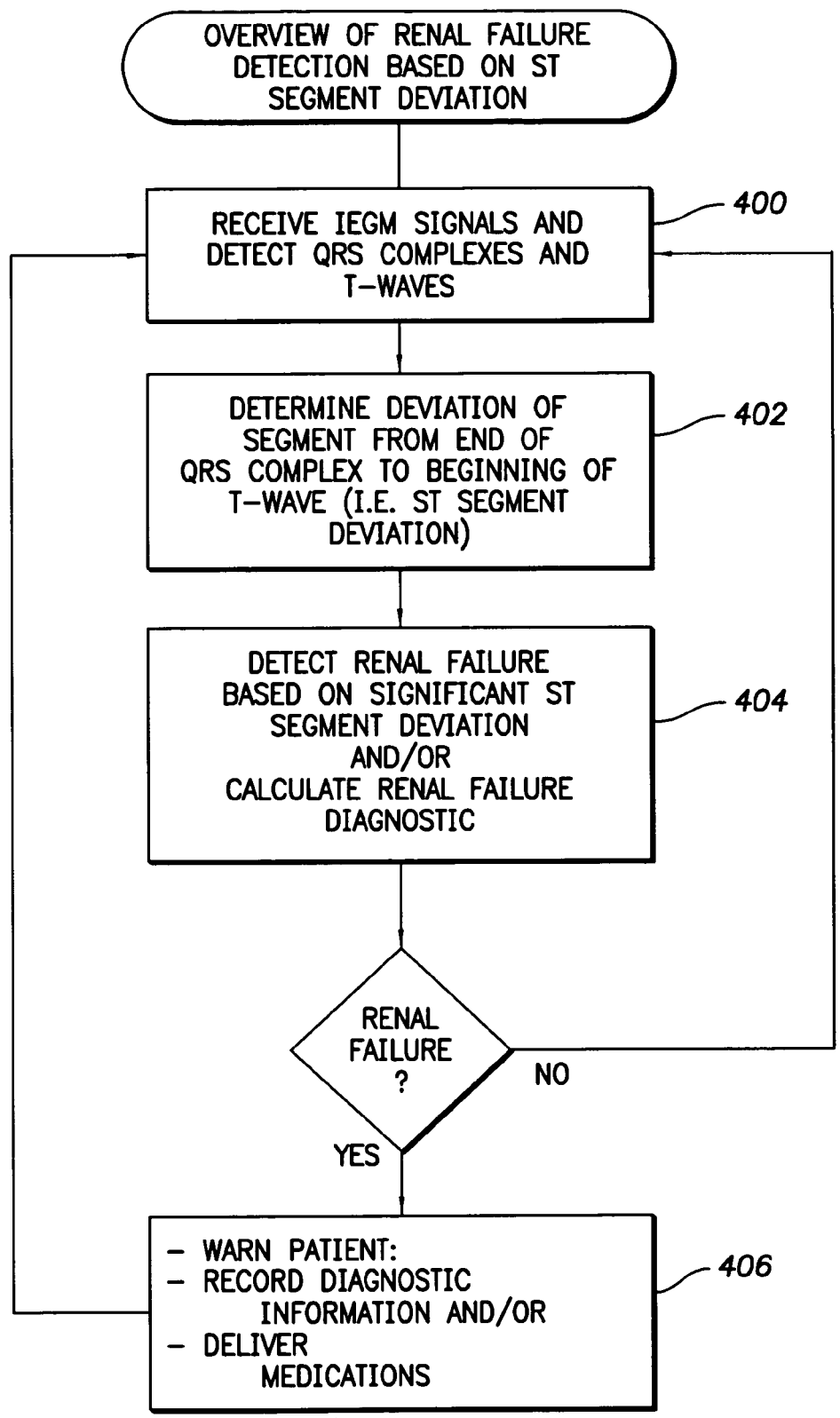
FIG. 9 is a flow chart providing an overview of an exemplary method performed by the device of FIG. 2 for detecting renal failure based on a deviation in ST segment elevation.

FIG. 9 provides an overview of a ST-deviation-based renal failure detection technique performed by the device of FIG. 2. Initially, at step 400, IEGM signals are received and QRS-complexes and T-waves are identified. At step 402, the elevation of the interval from the end of the QRS complex to the beginning of the T-wave is calculated. This interval is referred to as the ST segment; its elevation is referred to as the ST elevation; and any change in the ST elevation is referred to as the ST deviation. Conventional techniques for detecting ST segment elevation may be used. For example, detection of ST segment elevation is discussed in U.S. Pat. Nos. 6,016,443 and 6,256,538 to Ekwall. At step 404, renal failure is detected based upon observation of a significant deviation in the ST segment. A deviation in the ST is preferably calculated as a change in the average amplitude of the ST segment. Since the polarity of the IEGM signal is arbitrary, this may, in some cases, represent an increase in voltage of the ST segment and in other cases a decrease in voltage. It is the change in ST segment elevation that is important. As before, data from paced and sensed events should not be combined. ST segments may be referenced beat-by-beat to either the PQ or TP regions of the IEGM.

Additionally, or in the alternative, at step 404, the device calculates a renal failure burden based on ST deviation, which is representative of the risk of renal failure. In one example, the renal failure burden is a single metric value derived from ST deviation. If ST deviation is measured for diagnostic purposes only, steps 400-404 are preferably performed once an hour to calculate and record the hyperkalemic burden. If measured for detecting renal failure, steps 400-404 are preferably performed more often, e.g. once every 30 seconds. In any case, so long as no renal failure is detected, steps 400-404 are merely repeated. If renal failure is detected, however, the patient is warned of the renal failure, at step 406, and, if so equipped, the device automatically controls therapy in response to the renal failure.

FIG. 10 illustrates ST segment elevation. Briefly, FIG. 10 provides a stylized representation of an exemplary IEGM trace 408 for a single heartbeat for a patient suffering renal failure. The ST segment 410 is the interval from the end of the QRS complex 412 to the start of the T-wave 414. The duration of this interval is not of interest in this technique. However, its deviation, i.e. the extent to which its elevation changes over time is of interest. To calculate the elevation of an individual ST segment deviation, the device identifies a window 416 within the ST segment. The elevation of the ST segment (relative to a baseline voltage) within the window is denoted by reference numeral 418. The ST segment elevation 418 may be measured during a specified interval following the QRS complex 412, as shown. The interval may be, for example, 50 ms in duration, beginning 50 ms following the R wave of the QRS complex 412. For ventricular paced events, the interval may begin, for example, 80 ms following a V-pulse and extend for 50 ms. These are merely exemplary values. The ST segment elevation 418 may be quantified based on the mean of the ST segment sample.

FIG. 11 illustrates changes in ST segment elevation brought on by acute myocardial ischemia. A first exemplary IEGM trace 420 represents a heartbeat of a healthy patient. A second trace 422 illustrates the heartbeat for a patient suffering renal failure. As with other traces illustrated, the IEGM signals of FIG. 11 are exemplary representations of IEGM signals provided for illustrative purposes only. Comparing the two traces, the elevation of the ST-segment during renal failure 426 is greater than the elevation of the ST-segment without renal failure 424, i.e. there is a significant ST deviation.

ST segment deviation is the value used to detect renal failure. Preferably, any changes in the ST segment elevation from current baseline values are tracked. In one example, the device tracks a running average of the ST segment elevation (as derived from sensed events) and then, for each new heartbeat, the device compares the ST segment elevation for that heartbeat against the running average to calculate a ST deviation value for that heartbeat. Note that ST segment values need not be normalized based on heart rate. The value of ST deviation for the heartbeat is averaged over a number of heartbeats, e.g., eight to sixteen, and compared against a predetermined deviation-based threshold. If ST deviation exceeds its threshold (indicating a significant change in ST segment elevation), then renal failure is thereby indicated.

As disclosed in Kil et al. a significant deviation in ST elevation may also be indicative of ischemia, hypoglycemia or hyperglycemia. As further disclosed in Kil et al., during cardiac ischemia QTmax shortens and ΔQTend is substantially zero; during hypoglycemia both QTmax and QTend lengthen; and during hyperglycemia both ΔQTmax and ΔQTend are substantially zero. In accordance with the present invention, a significant ST elevation deviation in combination with a shortening of QTend distinguish a change in ST elevation deviation caused by any one of cardiac ischemia, hypoglycemia or hyperglycemia, from a change caused by renal failure.

Renal Failure Detection Based on QRS Width

Figure 12:
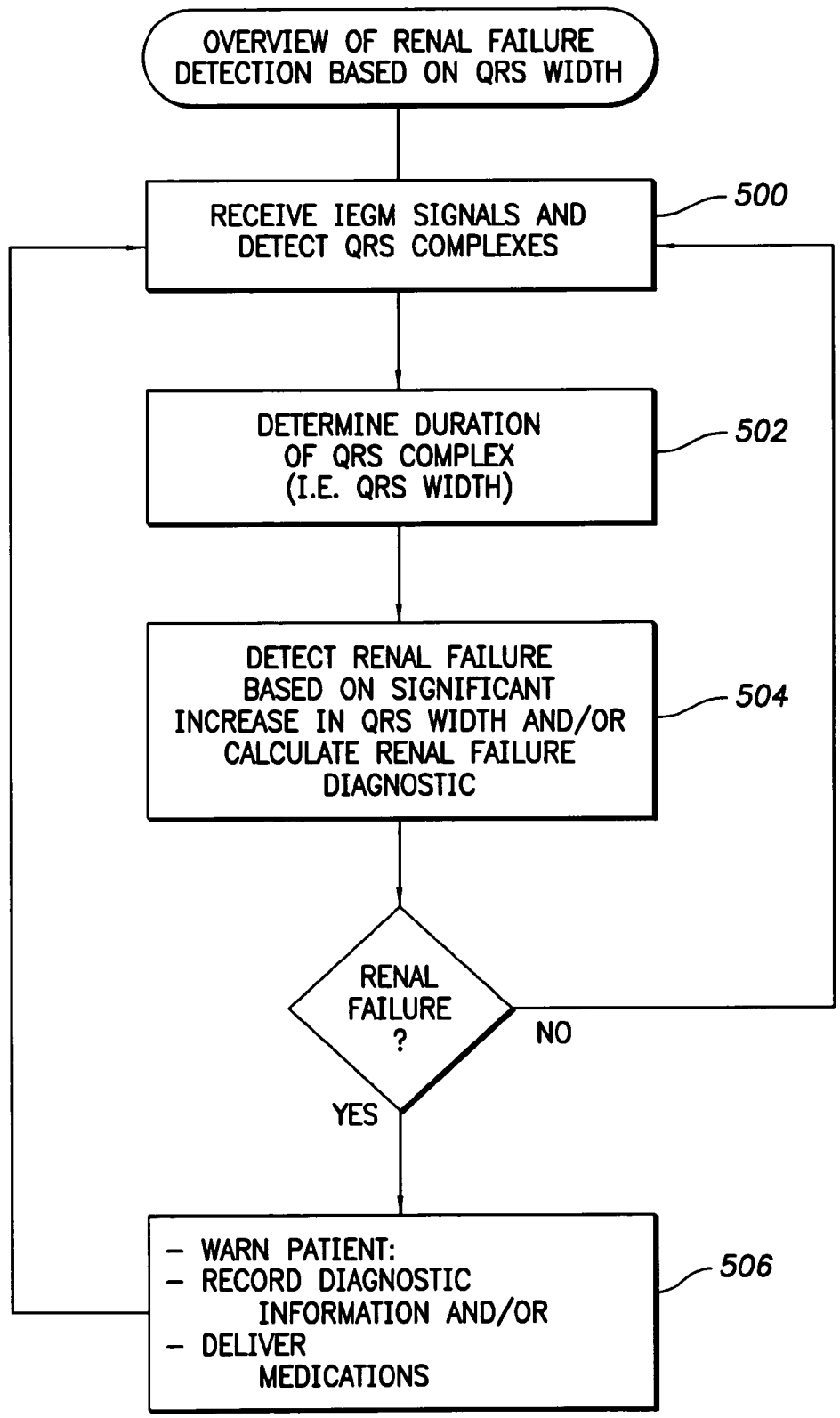
FIG. 12 is a flow chart providing an overview of an exemplary method performed by the device of FIG. 2 for detecting renal failure based on an increase in QRS width.

FIG. 12 provides an overview of a QRS-width-based hyperkalemia detection technique performed by the device of FIG. 2. Initially, at step 500, IEGM signals are received and QRS-complexes are identified. At step 502, the time from the beginning of the QRS complex to the end of the QRS complex is calculated. This duration is referred to as the QRS width. At step 504, renal failure is detected based upon observation of a significant increase in the QRS width. As before, data from paced and sensed events should not be combined.

Additionally, or in the alternative, at step 504, the device calculates a "renal failure burden" based on QRS width, which is representative of the proportion of time renal failure is detected. In one example, the renal failure burden is a numerical value representative of the extent to and/or time during which QRS width is larger than its running average. If QRS width is measured for diagnostic purposes only, steps 500-504 are preferably performed once an hour to calculate and record the renal failure burden. If measured for detecting renal failure, steps 500-504 are preferably performed more often, e.g. once every 30 seconds. In any case, so long as no renal failure is detected, steps 500-504 are merely repeated. If renal failure is detected, however, the patient is warned of the renal failure, at step 506, and, if so equipped, the device automatically controls therapy in response to the renal failure.

Figure 13:
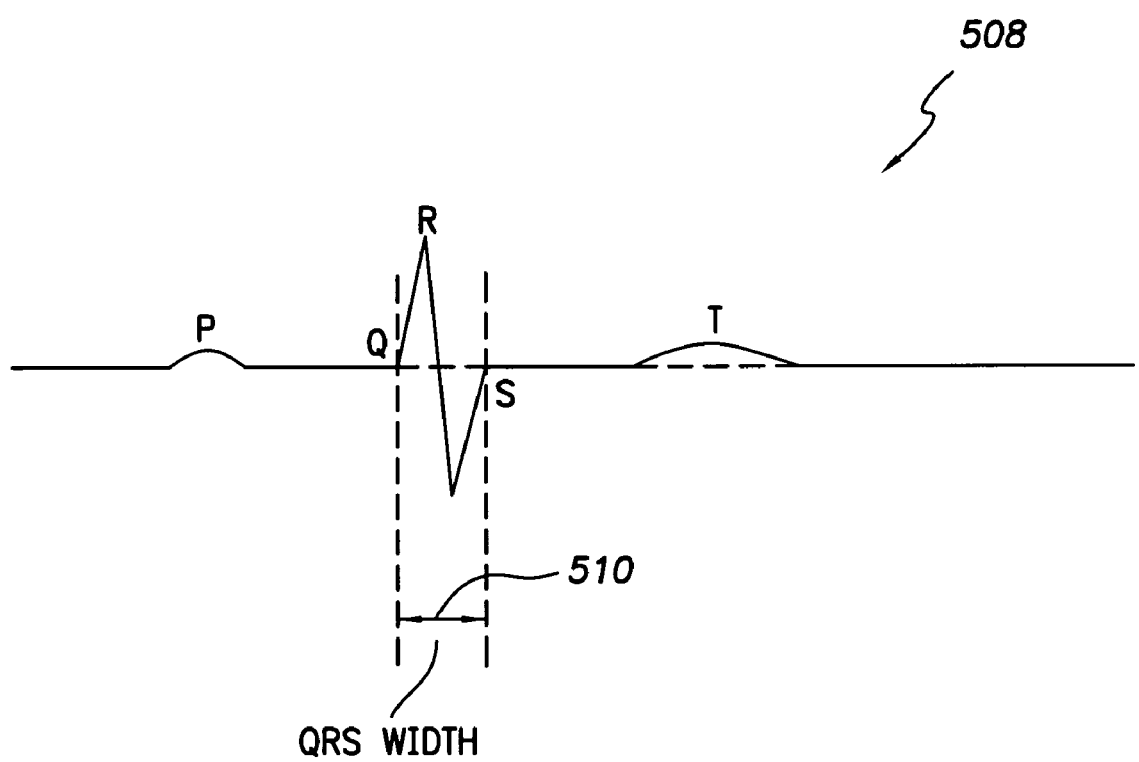
FIG. 13 is a graph providing a stylized representation of the IEGM of a single heartbeat illustrating QRS width.

FIG. 13 illustrates QRS width. Briefly, FIG. 13 provides a stylized representation of an exemplary IEGM trace 508 for a healthy single heartbeat. The QRS width 510 is the time between the beginning Q point and ending S point of the QRS complex.

Figure 14:
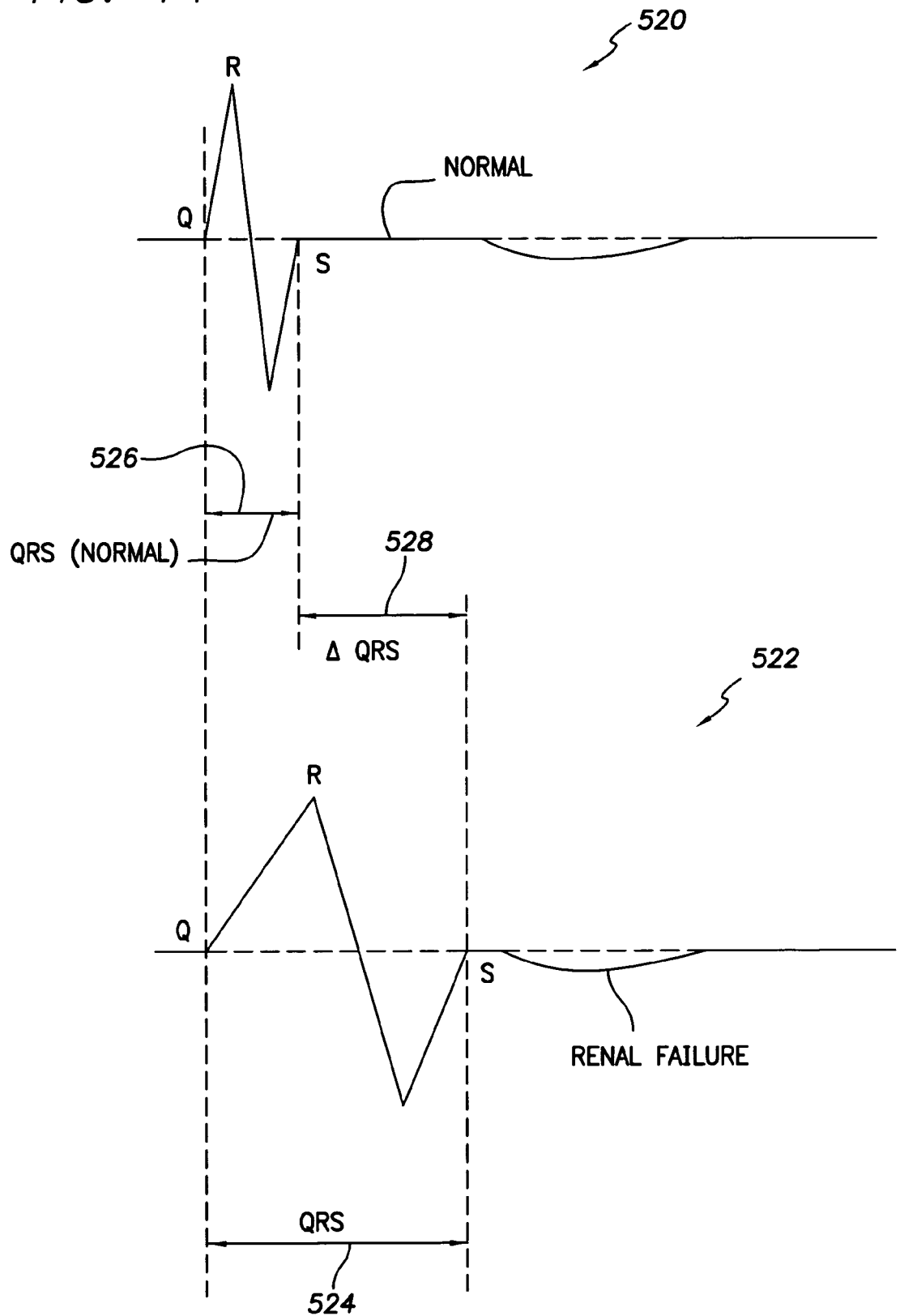
FIG. 14 is a graph providing exemplary representations of the IEGM of a single heart beat illustrating an increase in QRS width associated with renal failure.

FIG. 14 illustrates changes in QRS width brought on by renal failure. A first exemplary IEGM trace 520 represents a heartbeat of a healthy patient, i.e. one not subject to renal failure. A second trace 522 illustrates the heartbeat for a patient suffering renal failure. As with other traces illustrated, the IEGM signals of FIG. 14 are exemplary representations of IEGM signals provided for illustrative purposes only. For the purposes of renal failure detection, the QRS-width during renal failure 524 is larger than the QRS width without renal failure 526. Hence, a large positive value of ΔQRS width represents the amount of increase in QRS width. A negative value of ΔQRS width is associated with a decrease in QRS width, which would not be indicative of renal failure.

ΔQRS width is the value used to track renal failure. Preferably, any changes in the QRS width from current baseline values are tracked. In one example, the device tracks a running average of the QRS width (as derived from sensed events and normalized based on heart rate) and then, for each new heartbeat, the device compares the QRS width for that heartbeat against the running average to calculate a ΔQRS width value for that heartbeat. If the average exceeds the threshold, then the absolute value of ΔQRS width is also averaged over eight to sixteen heartbeats and compared against a predetermined ΔQRS width-based threshold. If ΔQRS width exceeds its respective threshold, then renal failure is thereby indicated.

The various thresholds are programmable values set, for example, based upon respective running averages. In one specific example, the threshold for ΔQRS width is set to 10% of the running average of the QRS width. As with the various other previously described techniques, alternative threshold comparison techniques may instead be used. Multiple thresholds may be defined, in some implementations, to trigger warning signals indicative of different levels of urgency. Routine experimentation may be performed to determine appropriate threshold levels.

Renal Failure Detection Based on PR Interval

Figure 15:
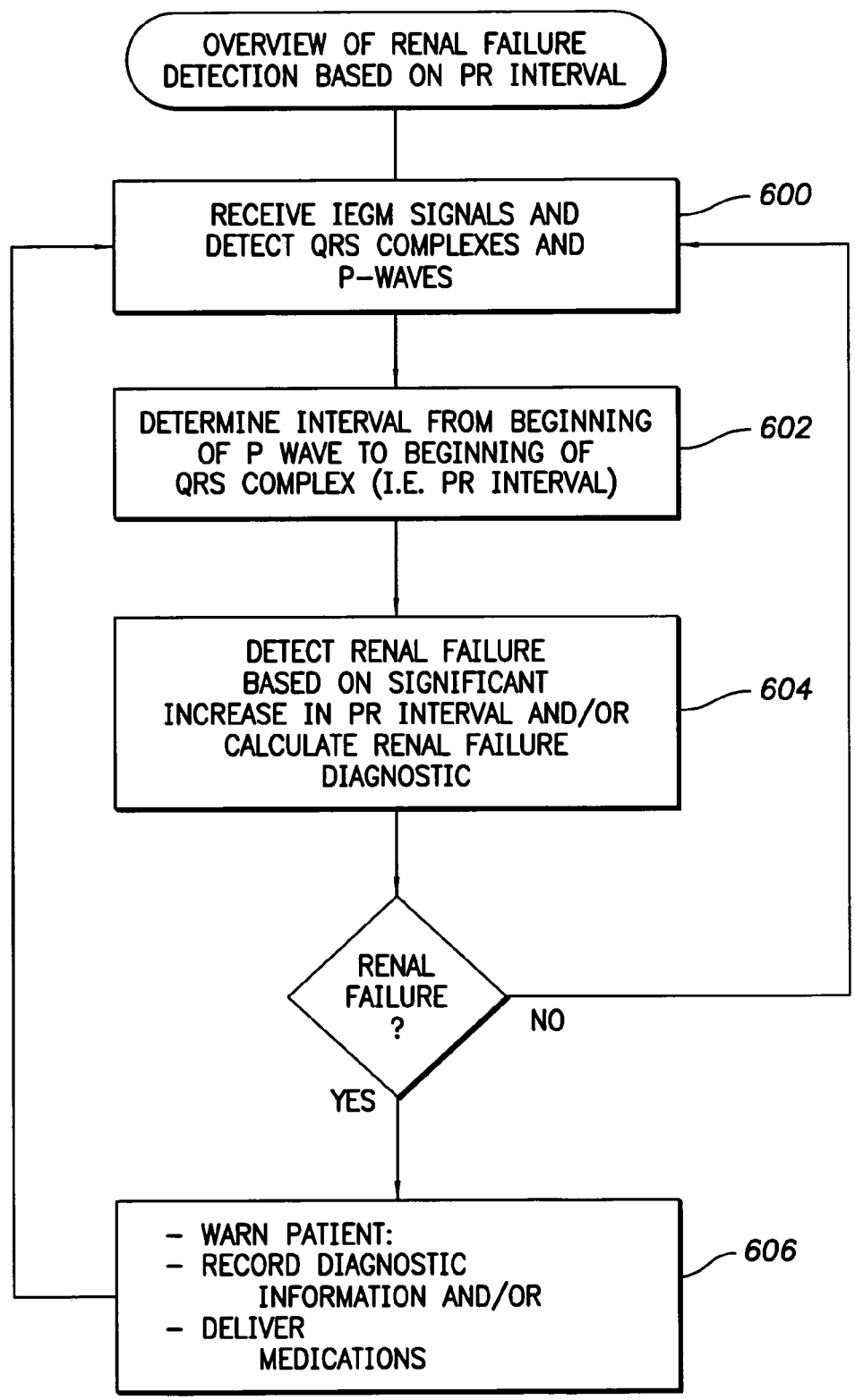
FIG. 15 is a flow chart providing an overview of an exemplary method performed by the device of FIG. 2 for detecting renal failure based on an increase in PR interval.

FIG. 15 provides an overview of a PR interval-based renal failure detection technique performed by the device of FIG. 2. Initially, at step 600, IEGM signals are received and QRS-complexes and T-waves are identified. At step 602, the interval between the onset of the P wave and the onset of the QRS complex is calculated. This interval is referred to as the PR interval. At step 604, renal failure is detected based upon observation of a significant increase in the PR interval. As before, data from paced and sensed events should not be combined.

Additionally, or in the alternative, at step 606, the device calculates a "renal failure burden" based on PR interval, which is representative of the proportion of time renal failure is detected. In one example, the renal failure burden is a numerical value representative of the extent to and/or time during which PR interval is larger than its running average. If PR interval is measured for diagnostic purposes only, steps 600-604 are preferably performed once an hour to calculate and record the hyperkalemic burden. If measured for detecting renal failure, steps 600-604 are preferably performed more often, e.g. once every 30 seconds. In any case, so long as no renal failure is detected, steps 600-604 are merely repeated. If renal failure is detected, however, the patient is warned of the renal failure, at step 606, and, if so equipped, the device automatically controls therapy in response to the renal failure.

Figure 16:
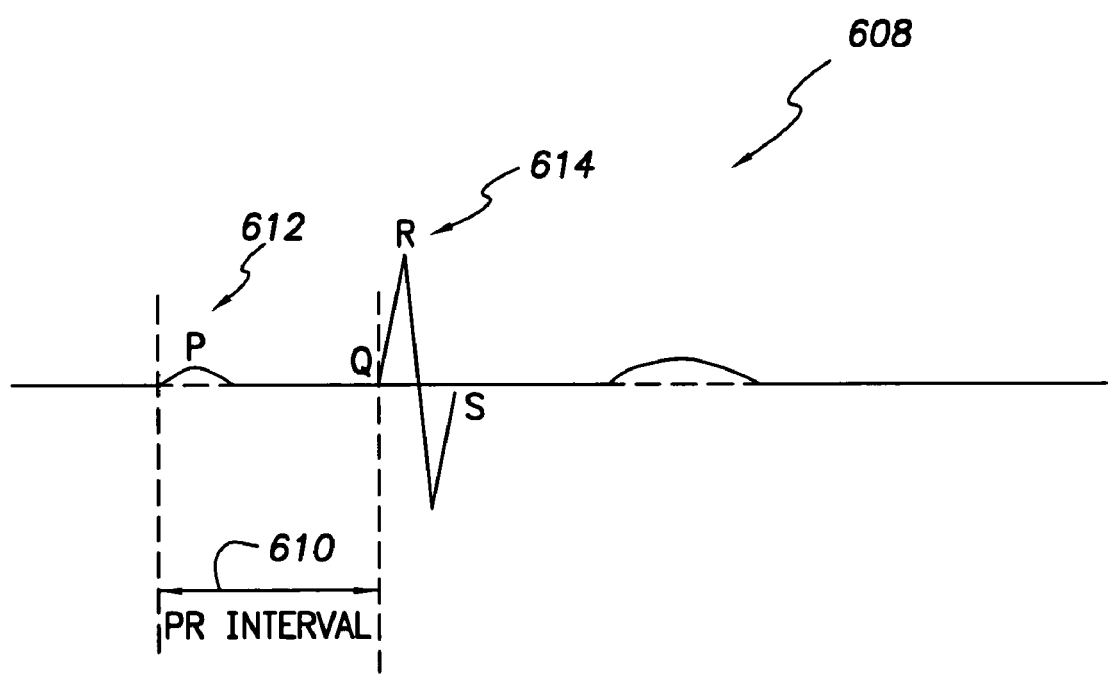
FIG. 16 is a graph providing a stylized representation of the IEGM of a single heartbeat illustrating the PR interval.

FIG. 16 illustrates PR interval. Briefly, FIG. 16 provides a stylized representation of an exemplary IEGM trace 608 for a single healthy heartbeat. The PR interval 610 is the time between the onset of the P wave 612 and the onset of the QRS complex 614.

Figure 17:
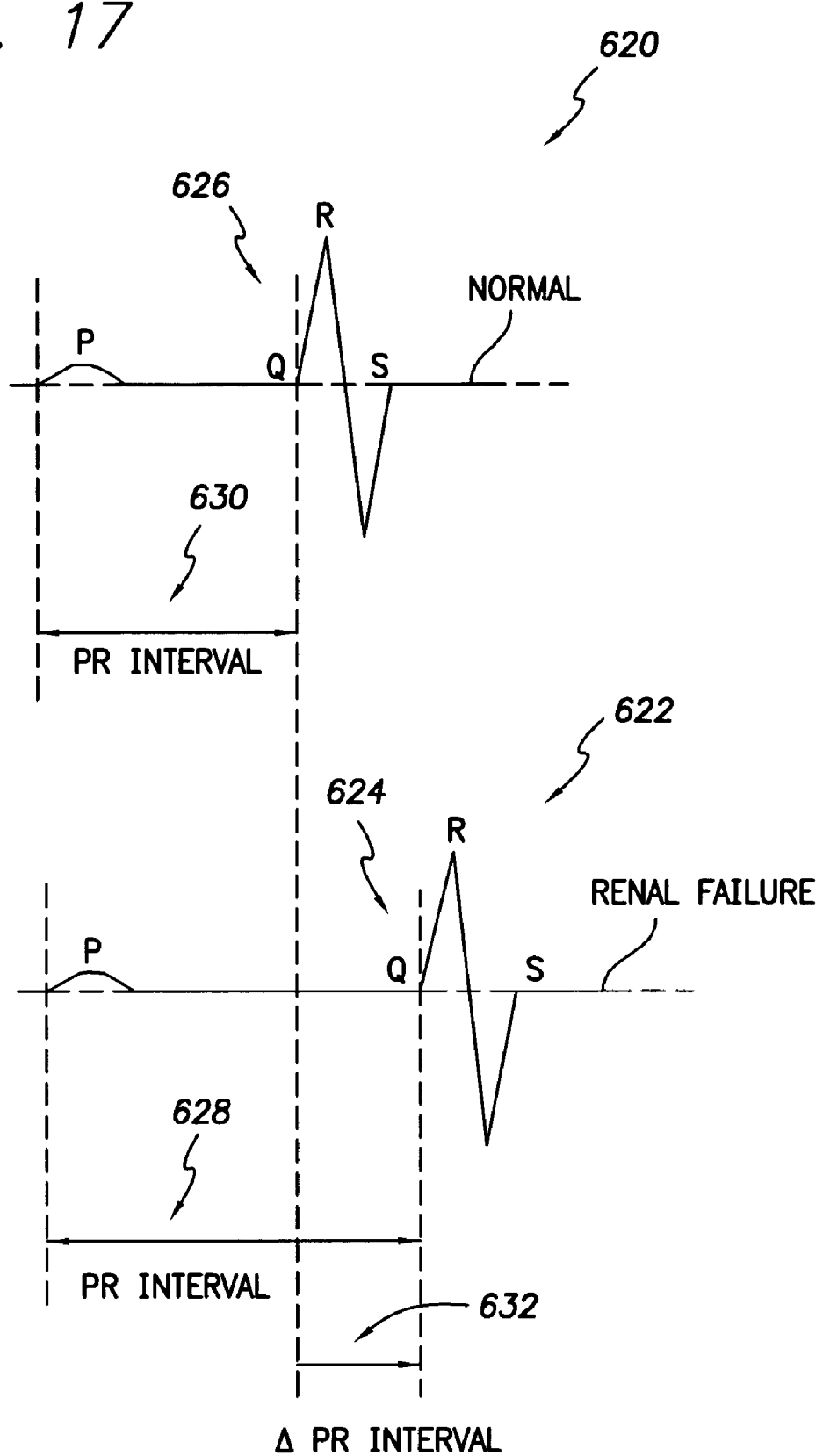
FIG. 17 is a graph providing exemplary representations of the IEGM of a single heart beat illustrating an increase in PR interval associated with renal failure.

FIG. 17 illustrates changes in PR interval brought on by renal failure. A first exemplary IEGM trace 620 represents a heartbeat of a healthy patient, i.e. one not subject to renal failure. A second trace 622 illustrates the heartbeat for a patient suffering renal failure. As with other traces illustrated, the IEGM signals of FIG. 17 are exemplary representations of IEGM signals provided for illustrative purposes only. For the purposes of renal failure detection, the beginning of the QRS complex 624 during renal failure occurs later than the corresponding beginning of the QRS complex 626 without renal failure. In other words, PR interval during renal failure 628 is greater than PR interval without renal failure 630. Hence, a large positive value of ΔPR interval 632 is observed, where ΔPR interval represents the amount of the increase in PR interval. A zero or negative value of ΔPR interval is associated with no change or a decrease in interval length, either of which would not be indicative of renal failure.

ΔPR interval is the value used to track renal failure. Preferably, any changes in the PR interval from current baseline values are tracked. In one example, the device tracks a running average of the PR interval (as derived from sensed events and normalized based on heart rate) and then, for each new heartbeat, the device compares the PR interval for that heartbeat against the running average to calculate a PR interval value for that heartbeat. The value of PR interval for the heartbeat is averaged over, e.g., eight to sixteen heartbeats and compared against a predetermined PR interval-based threshold. If the PR interval average exceeds its threshold (indicating a significant increase in PR interval), then renal failure is thereby indicated.

The various thresholds are programmable values set, for example, based upon respective running averages. In one specific example, the threshold for PR interval increase is set to 10% of the running average of the PR intervals. As with the other previously described techniques, alternative threshold comparison techniques may instead be used. Multiple thresholds may be defined, in some implementations, to trigger warning signals indicative of different levels of urgency. Routine experimentation may be performed to determine appropriate threshold levels.

Renal Failure Detection Based on T-wave Amplitude

Figure 18:
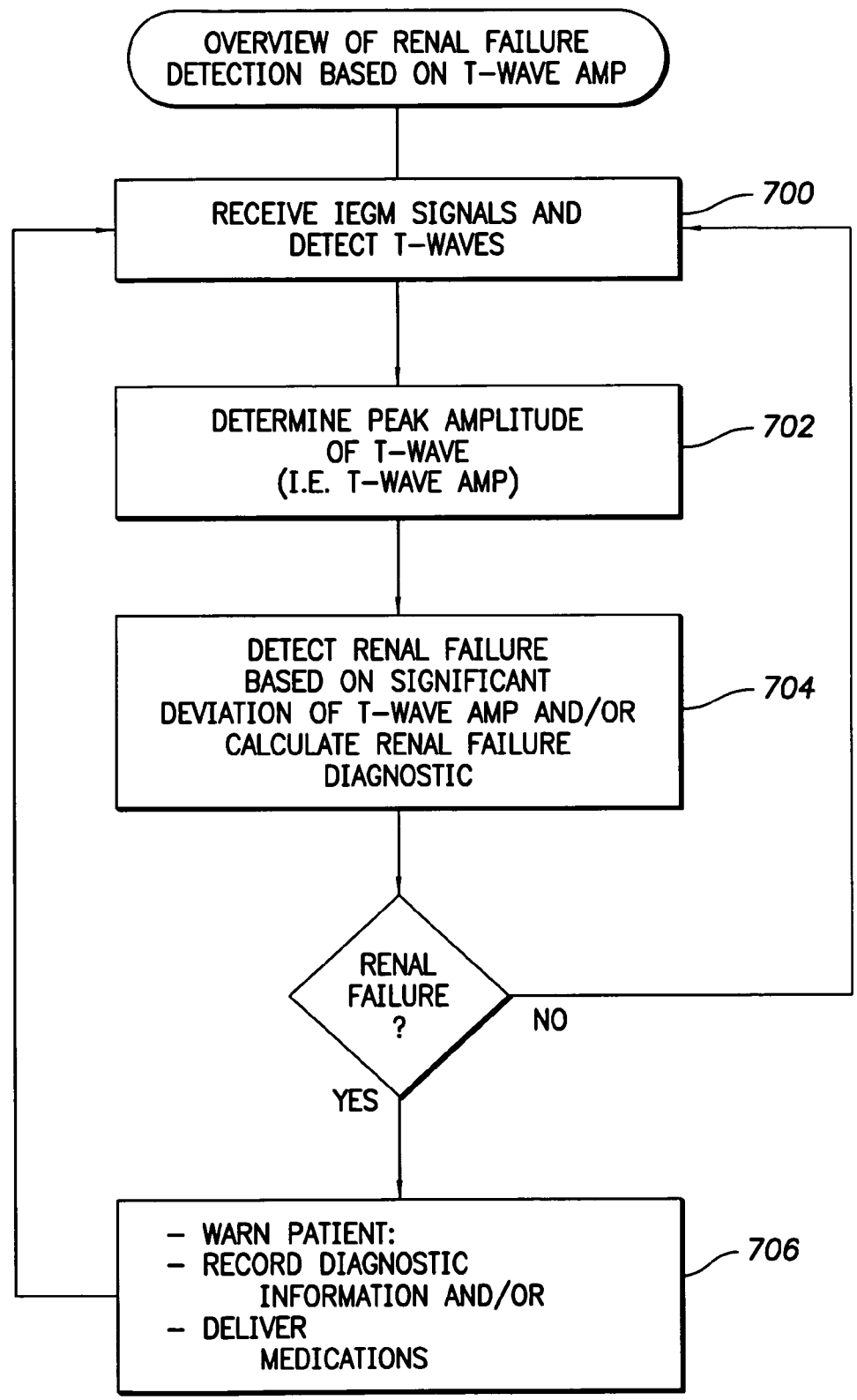
FIG. 18 is a flow chart providing an overview of an exemplary method performed by the device of FIG. 2 for detecting renal failure based on a deviation in T-wave amplitude.

FIG. 18 provides an overview of a T-wave amplitude based renal failure detection technique performed by the device of FIG. 2. Initially, at step 700, IEGM signals are received and T-waves are identified. The peak or maximum amplitude of the T-wave is calculated, at step 702. This amplitude is referred to as the T-wave amplitude. The maximum of the T-wave may be identified as the maximum point within a T-wave interval beginning 250 ms following the Q wave of the QRS complex and extending for 200 ms. At step 704, renal failure is detected based upon observation of a significant deviation in the T-wave amplitude. As before, data from paced and sensed events should not be combined.

Insofar as the detection of T-waves at step 700 is concerned, as previously mentioned the invention may exploit techniques set forth in Kroll. Certain techniques described therein are particularly well suited for detecting T-waves with a high degree of accuracy to permit precise detection of features of the T-wave (such as its peak) so as to achieve more precise measurement of QRS/T-wave intervals. The invention also may exploit T-wave detection techniques set forth within the aforementioned patent application to Min et al., which help prevent P-waves from being misinterpreted as T-waves on unipolar sensing channels.

Additionally, or in the alternative, at step 704, the device calculates a renal failure burden based on T-wave amplitude deviation, which is representative of the risk of renal failure. In one example, the renal failure burden is a single metric value derived from T-wave amplitude deviation. If T-wave amplitude is measured for diagnostic purposes only, steps 700-704 are preferably performed once an hour to calculate and record the renal failure burden. If measured for detecting renal failure, steps 700-704 are preferably performed more often, e.g. once every 30 seconds. In any case, so long as no renal failure is detected, steps 700-704 are merely repeated. If renal failure is detected, however, the patient is warned of the renal failure, at step 706, and, if so equipped, the device automatically controls therapy in response to the renal failure.

Figure 19:
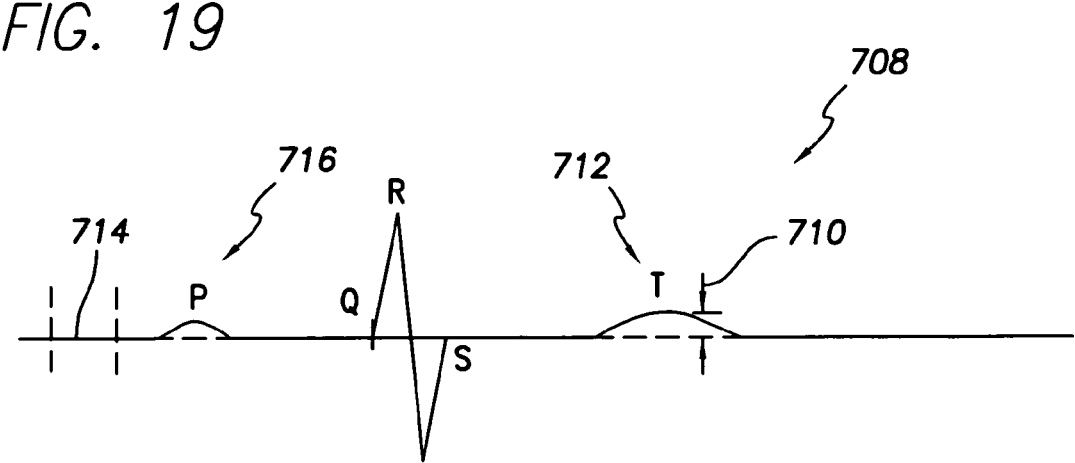
FIG. 19 is a graph providing a stylized representation of the IEGM of a single heartbeat illustrating the T-wave amplitude.

FIG. 19 illustrates T-wave amplitude. Briefly, FIG. 19 provides a stylized representation of an exemplary IEGM trace 708 for a single healthy heartbeat. The T-wave amplitude 710 is the peak or maximum of the absolute value of the difference between the T-wave 712 voltage and the baseline voltage of the IEGM signal. The baseline voltage 714 may be measured during an interval prior to the P-wave 716, as shown. The interval may be, for example, 50 milliseconds (ms) in duration, beginning 100 ms prior to the P-wave.

Figure 20:
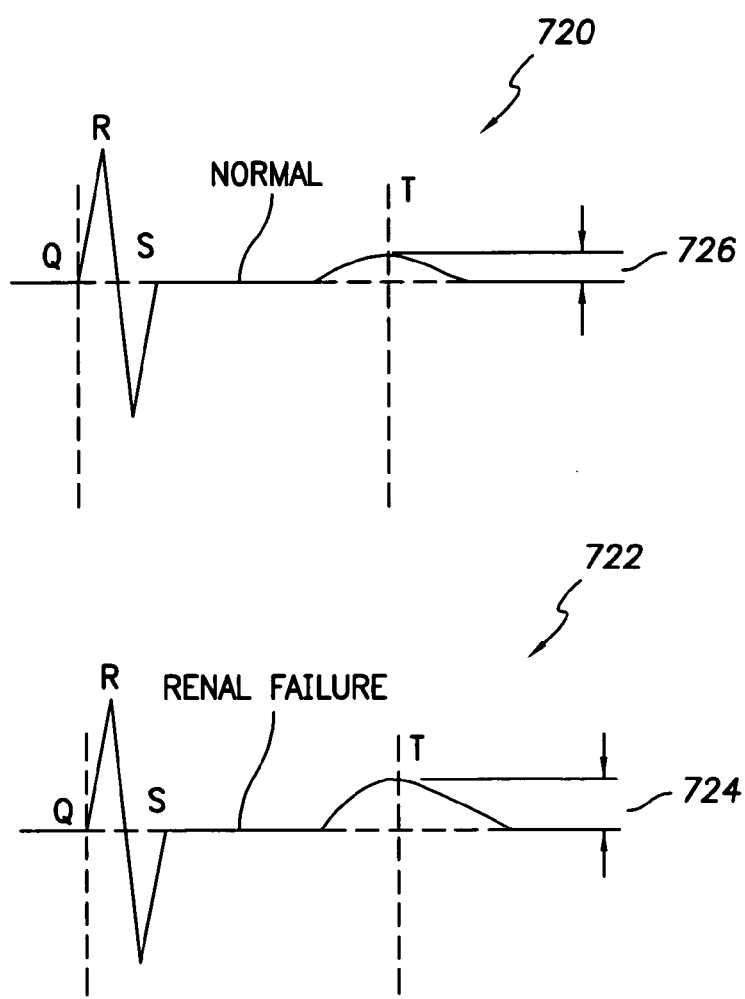
FIG. 20 is a graph providing exemplary representations of the IEGM of a single heart beat illustrating a deviation, in this case an increase, in T-wave amplitude associated with renal failure.

FIG. 20 illustrates changes in T-wave amplitude brought on by renal failure. A first exemplary IEGM trace 720 represents a heartbeat of a healthy patient, i.e. one not subject to renal failure. A second trace 722 illustrates the heartbeat for a patient suffering renal failure. As with other traces illustrated, the IEGM signals of FIG. 20 are exemplary representations of IEGM signals provided for illustrative purposes only. Comparing the two traces, the amplitude of the T-wave during renal failure 724 is greater than the amplitude of the T-wave without renal failure 726, i.e. there is a significant T-wave amplitude deviation.

T-wave amplitude deviation is the value used to detect renal failure. Preferably, any changes in the T-wave amplitude from current baseline values are tracked. In one example, the device tracks a running average of the T-wave amplitude (as derived from sensed events) and then, for each new heartbeat, the device compares the T-wave amplitude for that heartbeat against the running average to calculate a T-wave amplitude deviation value for that heartbeat. Note that T-wave amplitude values need not be normalized based on heart rate. The value of T-wave amplitude deviation for the heartbeat is averaged over a number of heartbeats, e.g., eight to sixteen, and compared against a predetermined deviation-based threshold. If T-wave amplitude deviation exceeds its threshold (indicating a significant change in T-wave amplitude), then renal failure is thereby indicated.

The various thresholds are programmable values set, for example, based upon respective running averages. As with the other techniques, alternative threshold comparison techniques may instead be used. Multiple thresholds may be defined, in some implementations, to trigger warning signals indicative of different levels of urgency. Routine experimentation may be performed to determine appropriate threshold levels.

It will be apparent from the foregoing that while particular forms of the invention have been illustrated and described, various modifications can be made without departing from the spirit and scope of the invention. For example, the stimulation device may use any one of various EGM configurations, such as unipolar, bipolar RA, RV, and LV leads. Accordingly, it is not intended that the invention be limited, except as by the appended claims.

What is claimed is:

1. An implantable medical system for detecting renal failure comprising:
    at least one lead comprising an electrode configured for placement within a patient in electrical contact with the patient's heart and operative to sense intracardiac electrograms;
    an implantable medical device adapted to be connected to the at least one lead and comprising:
        a tracking unit that tracks two different intervals between QRS complexes and corresponding T waves for each of at least two different PQRST complexes within an intracardiac electrogram sensed by the at least one lead; and
        a renal failure detection unit that detects renal failure if each of the two different intervals decrease by a respective amount, wherein the renal failure detection unit calculates a renal failure burden representative of a proportion of time renal failure is detected.

2. The system of claim 1 wherein one of the two different intervals is an interval between QRS-complexes and ends of corresponding T-waves (QTend intervals) and its respective amount is a percentage of a baseline QTend interval.

3. The system of claim 1 wherein one of the two different intervals is an interval between QRS-complexes and peaks of corresponding T-waves (QTmax intervals) and its respective amount is a percentage of a baseline QTmax interval.

4. The system of claim 1 further comprising a pulse generator that delivers a pacing pulse to the at least one lead to induce an evoked response element of the PQRST complexes.

5. An implantable medical system for detecting renal failure comprising:
    at least one lead comprising an electrode configured for placement within a patient in electrical contact with the patient's heart and operative to sense intracardiac electrograms;
    an implantable medical device adapted to be connected to the at least one lead and comprising:
        a tracking unit that tracks two different intervals between QRS complexes and corresponding T waves for each of at least two different PQRST complexes within an intracardiac electrogram sensed by the at least one lead, wherein the tracking unit also tracks at least one other morphological feature, distinct from the two different intervals, for each of the at least two different PQRST complexes within an intracardiac electrogram sensed by the lead; and
        a renal failure detection unit that detects renal failure if each of the two different intervals decrease by a respective amount and the at least one other morphological feature changes.

6. The system of claim 5 wherein the at least one other morphological feature comprises the elevation of a segment of a cardiac signal between QRS-complexes and corresponding T-waves (ST segment) and a change comprises an increase or decrease in the ST segment with respect to a baseline elevation.

7. The system of claim 5 wherein the at least one other morphological feature comprises the peak amplitude of a polarization event (T-wave amplitude) and a change comprises an increase or a decrease in the T-wave amplitude with respect to a baseline amplitude.

8. The system of claim 5 wherein the at least one other morphological feature comprises the interval between P-waves and corresponding QRS-complexes (PR interval) and a change comprises an increase in the PR interval with respect to a baseline interval.

9. The system of claim 5 wherein the at least one other morphological feature comprises the width of QRS-complexes and a change comprises an increase in the QRS width with respect to a baseline width.

* * * * *